US006180107B1

(12) United States Patent
Bayne et al.

(10) Patent No.: US 6,180,107 B1
(45) Date of Patent: Jan. 30, 2001

(54) VASCULAR ENDOTHELIAL CELL GROWTH FACTOR II

(75) Inventors: Marvin L. Bayne, Westfield, NJ (US); Gregory L. Conn, Beford Hill, NY (US); Kenneth A. Thomas, Jr., Chatham Burough, NJ (US)

(73) Assignee: Merck & Co., Inc., Rahway, NJ (US)

( * ) Notice: Under 35 U.S.C. 154(b), the term of this patent shall be extended for 0 days.

(21) Appl. No.: 09/038,199

(22) Filed: Mar. 10, 1998

Related U.S. Application Data

(60) Division of application No. 08/299,185, filed on Aug. 31, 1994, now Pat. No. 5,726,152, which is a continuation-in-part of application No. 08/000,834, filed on Jan. 5, 1993, now abandoned, which is a continuation of application No. 07/586,638, filed on Sep. 21, 1990, now abandoned.

(51) Int. Cl.$^7$ ................................................ A61K 38/18
(52) U.S. Cl. ........................................ 424/198.1; 530/399
(58) Field of Search ..................... 424/198.1; 435/69.1; 530/399

(56) References Cited

U.S. PATENT DOCUMENTS

| 5,194,596 | * | 3/1993 | Tischer et al. | 530/399 |
| 5,219,739 | * | 6/1993 | Tischer et al. | 435/69.4 |
| 5,338,840 | * | 8/1994 | Bayne et al. | 536/23.51 |

FOREIGN PATENT DOCUMENTS

| 0186084 | 12/1985 | (EP) . |
| 0259 953 | 3/1988 | (EP) . |
| 0399 816 | 11/1990 | (EP) . |
| WP 90/181364 | 1/1992 | (WO) . |
| WP89/088700 | 1/1992 | (WO) . |

OTHER PUBLICATIONS

Ferrara & Henzel, 'Pituitary Follicular Cells Secrete a Novel Heparin–Binding Growth Factor Specific for Vascular Endothelial Cells', Biochem. Biophys. Res. Comm. 161: 851–858, 1989.

Laemmli, 'Cleavage of Structural Proteins during the Assembly of the Head of Bacteriophage T4', Nature, 227: 680–684 (1970).

Saiki et al. 'EnzymaticAmplification of Beta–Globin Genomic Sequences and Restriction Site Analysis for Diagnosis of Sickle Cell Anemia' Science, 230: p. 1350–1354, (1985).

Frohman et al. 'Rapid production of full–length cDNAs from rare transcripts: . . . gene–specific oligonucleotide primer' Proc. Natl. Acad. Sci, USA 85, 8998–9002 (1988).

Tischer et al. 'Vascular Endothelial Growth Factor: A new member of the platelet derived growth factor gene Family', Biochem. & Biophysical Res. Comm. 165: 1198, (1989).

Conn et al. Proc. Natl. Acad. Sci. USA 87: p. 1323–1327 (1990).

Keck et al. 'Vascular Permeability Factor an Endothelial Cell Mitogen Related to PDGF', Science, 246: p. 1309–1312 (1989).

Bowie et al.'Deciphering the Message in Protein Sequences: Tolerance to Amino Acid Substitutions', Science 247: p. 1306–1310 (1989).

Conn, Endothelial Cell Growth Factors, Yeshiva University, 1987.

Gospodarowicz et al. 'Isolation and characterization of a vascular endothelial cell mitogen produced by pituitary–derived folliculo stellate cells', Proc. Natl. Acad. Sci. USA 86: p. 7311–7315 (1989).

Joukov et al. 'A Novel vascular endothelial growth factor. VEGF–C, . . . receptor tyrosine kinases', Embo. J., vol. 15 pp. 290–298 (1996).

Leung et al. (1989) Science 246, p. 1306–1309.*
Conn et al. (1990) PNAS USA 87, p. 2628–2632.*

\* cited by examiner

Primary Examiner—Lorraine Spector
(74) Attorney, Agent, or Firm—J. Mark Hand; Jack L. Tribble

(57) ABSTRACT

Vascular endothelial cell growth factor II is purified from the culture media used to maintain mammalian glioma cells. The protein is a heterodimer, stimulates mitogenesis of mammalian vascular endothelial cells and is useful for the promotion of vascular development and repair. This unique growth factor is also useful in the promotion of tissue repair.

5 Claims, 32 Drawing Sheets

```
                                    ┌─────────── p5-15 ───────────
    A ACC ATG AAC TTT CTG CTC TCT TGG GTG CAC TGG ACC CTG GCT TTA CTG TAC CTC CAC CAT
                                    1                                              20
      MET-ASN-PHE-LEU-LEU-SER-TRP-VAL-HIS-TRP-THR-LEU-ALA-LEU-LEU-TYR-LEU-HIS-HIS-

┌─────────── p5-15 ───────────
    GCC AAG TGG TCC CAG GCT GCA CCC ACG ACA GAA GGG GAG CAG AAA GCC CAT GAA GTG GTG
    21                                                                              40
      ALA-LYS-TRP-SER-GLN-ALA-[ALA-PRO-THR-THR-GLU-GLY-GLU-GLN-LYS-ALA-HIS-GLU-VAL-VAL-
                                              ↑ ↑ ↑ ↑ ↑ ↑ ↑ ↑ ↑ ↑ ↑ ↑ ↑ ↑
                                              └──── L13 ────┘└── L16 ──

┌─── p4238 ───┐
                                    ┌─────────── p5-15 ─────────────
    AAG TTC ATG GAC GTC TAC CAG CGC AGC TAT TGC CGT CCG ATT GAG ACC CTG GTG GAC ATC
    41                                                                              60
      LYS-PHE-MET-ASP-VAL-TYR-GLN-ARG-SER-TYR-CYS-ARG-PRO-ILE-GLU-THR-LEU-VAL-ASP-ILE-
                                    ↑ ↑ ↑ ↑ ↑ ↑ ↑ ↑ ↑ ↑ ↑ ↑ ↑ ↑ ↑ ↑ ↑ ↑ ↑ ↑
                                    └──────────── L46 ─────────────┘

FIG. 4E
```

```
                                              p4238
 TTC CAG GAG TAC CCC GAT GAG ATA TTC AAG CCG TCC TGT GTG CCC CTA ATG
  61                                  70                            80
 PHE-GLN-GLU-TYR-PRO-ASP-GLU-ILE-PHE-LYS-PRO-SER-CYS-VAL-PRO-LEU-MET-
      ↑  ↑  ↑  ↑  ↑
                                              L46 p4238
 CGG TGT GCG GGC TGC TGC AAT GAT GAA GCC CTG GAG TGC GTG CCC ACG TCG GAG AGC AAC
  81                                  90                           100
 ARG-CYS-ALA-GLY-CYS-CYS-ASN-ASP-GLU-ALA-LEU-GLU-CYS-VAL-PRO-THR-SER-GLU-SER-ASN-
                                              L46 p4238
 GTC ACT ATG CAG ATC ATG CGG ATC AAA CCT CAC CAA AGC CAG CAC ATA GGA GAG ATG AGC
 101                                 110                           120
 VAL-THR-MET-GLN-ILE-MET-ARG-ILE-LYS-PRO-HIS-GLN-SER-GLN-HIS-ILE-GLY-GLU-MET-SER-
                                              L46
```

FIG. 4F

```
                                          pW-3
CGT ACT TGC AGA TGT GAC AAG CCA AGG CGG TGA
181                                   190
ARG-THR-CYS-ARG-CYS-ASP-LYS-PRO-ARG-ARG  *
```

FIG. 4H

```
                                     ─── 202 ───                                          ─── pCV2 ───
ATG CTG GCC ATG AAG CTG TTC ACT TGC TTC TTG CAG GTC CTA GCT GGG TTG
MET-LEU-ALA-MET-LYS-LEU-PHE-THR-CYS-PHE-LEU-GLN-VAL-LEU-ALA-GLY-LEU-
 1                              10

─── pCV2 ───
GCT GTA CAC TCC CAG GGG GCC CTG TCT GCT GGG AAC AAC TCA ACA GAA ATG GAA GTG GTG
ALA-VAL-HIS-SER-GLN-GLY-ALA-LEU-SER-ALA-GLY-ASN-SER-THR-GLU-MET-GLU-VAL-VAL-
                   20                              30        [ASN]
                                                              [L44]

─── pCV2 ───
CCT TTC AAT GAA GTG TGG GGC CGC AGC TAC TGC CGG CCA ATG GAG AAG CTG GTG TAC ATT
PRO-PHE-ASN-GLU-VAL-TRP-GLY-ARG-SER-TYR-CYS-ARG-PRO-MET-GLU-LYS-LEU-VAL-TYR-ILE-
          40                              50
          [L44]

FIG. 4I
```

```
——————————— pCV2 ———————————
GCA GAT GAA CAC CCT AAT GAA GTG TCT CAT ATA TTC AGT CCG TCA TGT GTC CTT CTG AGT
ALA-ASP-GLU-HIS-PRO-ASN

ATG CTG GCC ATG AAG CTG TTC ACT TGC TTC TTG CAG GTC CTA GCT GGG TTG
MET-LEU-ALA-MET-LYS-LEU-PHE-THR-CYS-PHE-LEU-GLN-VAL-LEU-ALA-GLY-LEU-
1                              10

GCT GTA CAC TCC CAG GGG GCC CTG TCT GCT GGG AAC AAC TCA ACA GAA ATG GAA GTG GTG
ALA-VAL-HIS-SER-GLN-GLY-ALA-LEU-SER-ALA-GLY-ASN-ASN-SER-THR-GLU-MET-GLU-VAL-VAL-
     20                              30

CCT TTC AAT GAA GTG TGG GGC CGC AGC TAC TGC CGG CCA ATG GAG AAG CTG GTG TAC ATT
PRO-PHE-ASN-GLU-VAL-TRP-GLY-ARG-SER-TYR-CYS-ARG-PRO-MET-GLU-LYS-LEU-VAL-TYR-ILE-
     40                              50

GCA GAT GAA CAC CCT AAT GAA GTG TCT CAT ATA TTC AGT CCG TCA TGT GTC CTT CTG AGT
ALA-ASP-GLU-HIS-PRO-ASN-GLU-VAL-SER-HIS-ILE-PHE-SER-PRO-SER-CYS-VAL-LEU-LEU-SER-
     60                              70

FIG. 4L

```
————————————— pCU2.1 —————————————
CGC TGT AGT GGC TGC TGT GGT GAC GAG GGT CTG CAC TGT GTG GCG CTA AAG ACA GCC AAC
                           80                              90
ARG-CYS-SER-GLY-CYS-CYS-GLY-ASP-GLU-GLY-LEU-HIS-CYS-VAL-ALA-LEU-LYS-THR-ALA-[ASN]-

————————————— pCU2.1 —————————————
ATC ACT ATG CAG ATC TTA AAG ATT CCC CCC AAT CGG GAT CCA CAT TCC TAC GTG GAG ATG
                          100                              110
ILE-THR-MET-GLN-ILE-LEU-LYS-ILE-PRO-PRO-ASN-ARG-ASP-PRO-HIS-SER-TYR-VAL-GLU-MET-

————————————— pCU2.1 —————————————
ACA TTC TCT CAG GAT GTA CTC TGC GAA TGC AGG CCT ATT CTG GAG ACG ACA AAG GCA GAA
                         120                              130
THR-PHE-SER-GLN-ASP-VAL-LEU-CYS-GLU-CYS-ARG-PRO-ILE-LEU-GLU-THR-THR-LYS-ALA-GLU-

→
AGG TAA
138
ARG  *
```

FIG. 4M

```
|---------------- p4238 ----------------|
TTC CAG GAG TAC CCC GAT GAG ATA GAG TAT ATC TTC AAG CCG TCC TGT GTG CCC CTA ATG
 61                                      70                                   80
PHE-GLN-GLU-TYR-PRO-ASP-GLU-ILE-GLU-TYR-ILE-PHE-LYS-PRO-SER-CYS-VAL-PRO-LEU-MET-
                        ↑   ↑   ↑   ↑
                        ↑
|---------------- L46 ----------------|

|---------------- p4238 ----------------|
CGG TGT GCG GGC TGC TGC AAT GAT GAA GCC CTG GAG TGC GTG CCC ACG TCG GAG AGC AAC
 81                                      90                                  100
ARG-CYS-ALA-GLY-CYS-CYS-ASN-ASP-GLU-ALA-LEU-GLU-CYS-VAL-PRO-THR-SER-GLU-SER-|ASN|
|---------------- L46 ----------------|

|---------------- p4238 ----------------|
GTC ACT ATG CAG ATC ATG CGG ATC AAA CCT CAC CAA AGC CAG CAC ATA GGA GAG ATG AGC
101                                      110                                 120
VAL-THR-MET-GLN-ILE-MET-ARG-ILE-LYS-PRO-HIS-GLN-SER-GLN-HIS-ILE-GLY-GLU-MET-SER-
|---------------- L46 ----------------|
```

FIG. 5A

```
|------- pCV2 -------|
|------------------- 202 -------------------|
ATG CTG GCC ATG AAG CTG TTC ACT TGC TTC TTG CAG GTC CTA GCT GGG TTG
 1                                    10
MET-LEU-ALA-MET-LYS-LEU-PHE-THR-CYS-PHE-LEU-GLN-VAL-LEU-ALA-GLY-LEU-

GCT GTA CAC TCC CAG GGG GCC CTG TCT GCT GGG AAC AAC TCA ACA GAA ATG GAA GTG GTG
         20                                    30
ALA-VAL-HIS-SER-GLN-GLY-ALA-LEU-SER-ALA-GLY-ASN-ASN-SER-THR-GLU-MET-GLU-VAL-VAL-
                        |------- pCV2 -------|            [L44]

CCT TTC AAT GAA GTG TGG GGC CGC AGC TAC TGC CGG CCA ATG GAG AAG CTG GTG TAC ATT
         40                                    50
PRO-PHE-ASN-GLU-VAL-TRP-GLY-ARG-SER-TYR-CYS-ARG-PRO-MET-GLU-LYS-LEU-VAL-TYR-ILE-
                        |------- pCV2 -------|
       [L44]

FIG. 6
```

```
—pCU2—
GCA GAT GAA CAC CCT AAT GAA GTG TCT CAT ATA TTC AGT CCG TCA TGT GTC CTT CTG AGT
                    60                                70
ALA-ASP-GLU-HIS-PRO-ASN-GLU-VAL-SER-HIS-ILE-PHE-SER-PRO-SER-CYS-VAL-LEU-LEU-SER-
                                                    L50

—pCU2—
CGC TGT AGT GGC TGC TGT GGT GAC GAG GGT CTG CAC TGT GTG GCG CTA AAG ACA GCC AAC
              80                                90
ARG-CYS-SER-GLY-CYS-CYS-GLY-ASP-GLU-GLY-LEU-HIS-CYS-VAL-ALA-LEU-LYS-THR-ALA-ASN-
                            L50

—pCU2—
ATC ACT ATG CAG ATC TTA AAG ATT CCC CCC AAT CGG GAT CCA CAT TCC TAC GTG GAG ATG
              100                                110
ILE-THR-MET-GLN-ILE-LEU-LYS-ILE-PRO-PRO-ASN-ARG-ASP-PRO-HIS-SER-TYR-VAL-GLU-MET-
        L35                                                              [L44]

FIG. 6A
```

```
─────────────────────── pCU2 ───────────────────────
ACA TTC TCT CAG GAT GTA CTC TGC GAA TGC AGG CCT ATT CTG GAG ACG ACA AAG GCA GAA
                              128                                  130
THR-PHE-SER-GLN-ASP-VAL-LEU-CYS-GLU-CYS-ARG-PRO-ILE-LEU-GLU-THR-THR-LYS-ALA-GLU-
           ↑ ↑ ↑                              [L44]                  ↑ ↑ ↑
                                                                     ↓

─────────────────────── pCU2 ───────────────────────
AGG AGG AAA ACC AAG AGC AAA ACC CCA CAG ACT GAG GAA CCC CAC
                    140                       150
ARG-ARG-LYS-THR-LYS-GLY-LYS-LYS-ARG-LYS-GLN-SER-LYS-GLN-SER-LYS-THR-PRO-GLN-THR-GLU-GLU-PRO-HIS-
                                                              ↑ ↑ ↑ ↑ ↑ ↑ ↑ ↑
                                                              ↓       L26

CTG TGA
158          ↑↑
LEU *        ↑↑
```

FIG. 6B

```
                                                                    ──── pCU2.1 ────

──────────────────── 202 ────────────────────
ATG CTG GCC ATG AAG CTG TTC ACT TGC TTC TTG CAG GTC CTA GCT GGG TTG
 1                              10
MET-LEU-ALA-MET-LYS-LEU-PHE-THR-CYS-PHE-LEU-GLN-VAL-LEU-ALA-GLY-LEU-

──────────────────── pCU2.1 ────────────────────
GCT GTA CAC TCC CAG GGG GCC CTG TCT GCT GGG AAC AAC TCA ACA GAA ATG GAA GTG GTG
                20                                30
ALA-VAL-HIS-SER-GLN-GLY-ALA-LEU-SER-ALA-GLY-ASN-ASN-SER-THR-GLU-MET-GLU-VAL-VAL-

──────────────────── pCU2.1 ────────────────────
CCT TTC AAT GAA GTG TGG GGC CGC AGC TAC TGC CGG CCA ATG GAG AAG CTG TAC ATT
                40                                50
PRO-PHE-ASN-GLU-VAL-TRP-GLY-ARG-SER-TYR-CYS-ARG-PRO-MET-GLU-LYS-LEU-TYR-ILE-

──────────────────── pCU2.1 ────────────────────
GCA GAT GAA CAC CCT AAT GAA GTG TCT CAT ATA TTC AGT CCG TCA TGT GTC CTT CTG AGT
                60                                70
ALA-ASP-GLU-HIS-PRO-ASN-GLU-VAL-SER-HIS-ILE-PHE-SER-PRO-SER-CYS-VAL-LEU-LEU-SER-
```

FIG. 7

|———————————————————— pCV2.1 ————————————————————|

CGC TGT AGT GGC TGT TGT GGT

VASCULAR ENDOTHELIAL CELL GROWTH FACTOR II

RELATED APPLICATIONS

This application is a divisional of application No. 08/299,185, filed Aug. 31, 1994, issued as U.S. Pat. No. 5,726,152, which is a continuation-in-part of application No. 08/000,834, filed Jan. 5, 1993, abandoned, which is a continuation of application No. 07/586,638, filed Sep. 21, 1990, abandoned.

BACKGROUND OF THE INVENTION

A new class of cell-derived dimeric mitogens with apparently restricted specificity for vascular endothelial cells has recently been identified and generally designated vascular endothelial cell growth factor (VEGF). The mitogen has been purified from: conditioned growth media of rat glioma cells, [Conn et al., *Proc. Natl. Acad. Sci. USA* 87: 2628–2632 (1990)]; conditioned growth media of bovine pituitary folliculo stellate cells [Ferrara and Henzel, *Biochem. Biophys. Res. Comm.* 161: 851–858 (1989) and Gospodarowicz et al., *Proc. Natl. Acad. Sci. USA* 86: 7311–7315 (1989)]. Vascular endothelial growth factor I (VEGF I) is a homodimer with an apparent molecular mass of 46 kDa, with each subunit having an apparent molecular mass of 23 kDa. VEGF I has distinct structural similarities to platelet-derived growth factor (PDGF), a mitogen for connective tissue cells but not vascular endothelial cells from large vessels.

SUMMARY OF THE INVENTION

Vascular endothelial cell growth factor II is purified from the culture media used to maintain mammalian glioma cells. The protein is a heterodimer and stimulates mitogenesis of mammalian vascular endothelial cells and is useful for the promotion of vascular development and repair. This unique growth factor is also useful in the promotion of tissue repair. The present invention provides a novel vascular endothelial growth factor II (VEGF II) free of other proteins and provides a procedure for its purification. VEGF II is also provided which stimulates endothelial cells for induction of blood vessel growth, vascular repair, the production of artificial blood vessels and tissue repair.

BRIEF DESCRIPTION OF THE DRAWINGS

FIG. 5 and FIGS. 5A through 5C. Full length amino acid residue protein translation product and its cDNA coding sequence for VEGF II A subunit plus polypeptide cleavage products used to determine the amino acid sequence.

FIG. 6 and FIGS. 6A through 6B. Full length 158 amino acid residue protein translation product and its cDNA coding sequence for the mature 135 amino acid form of VEGF II B subunit plus polypeptide cleavage products used to determine the amino acid sequence.

FIG. 7 and FIG. 7A. Full length 138 amino acid residue protein translation product and its cDNA coding sequence for the mature 115 amino acid form of VEGF II B subunit.

DETAILED DESCRIPTION

Figure 1:
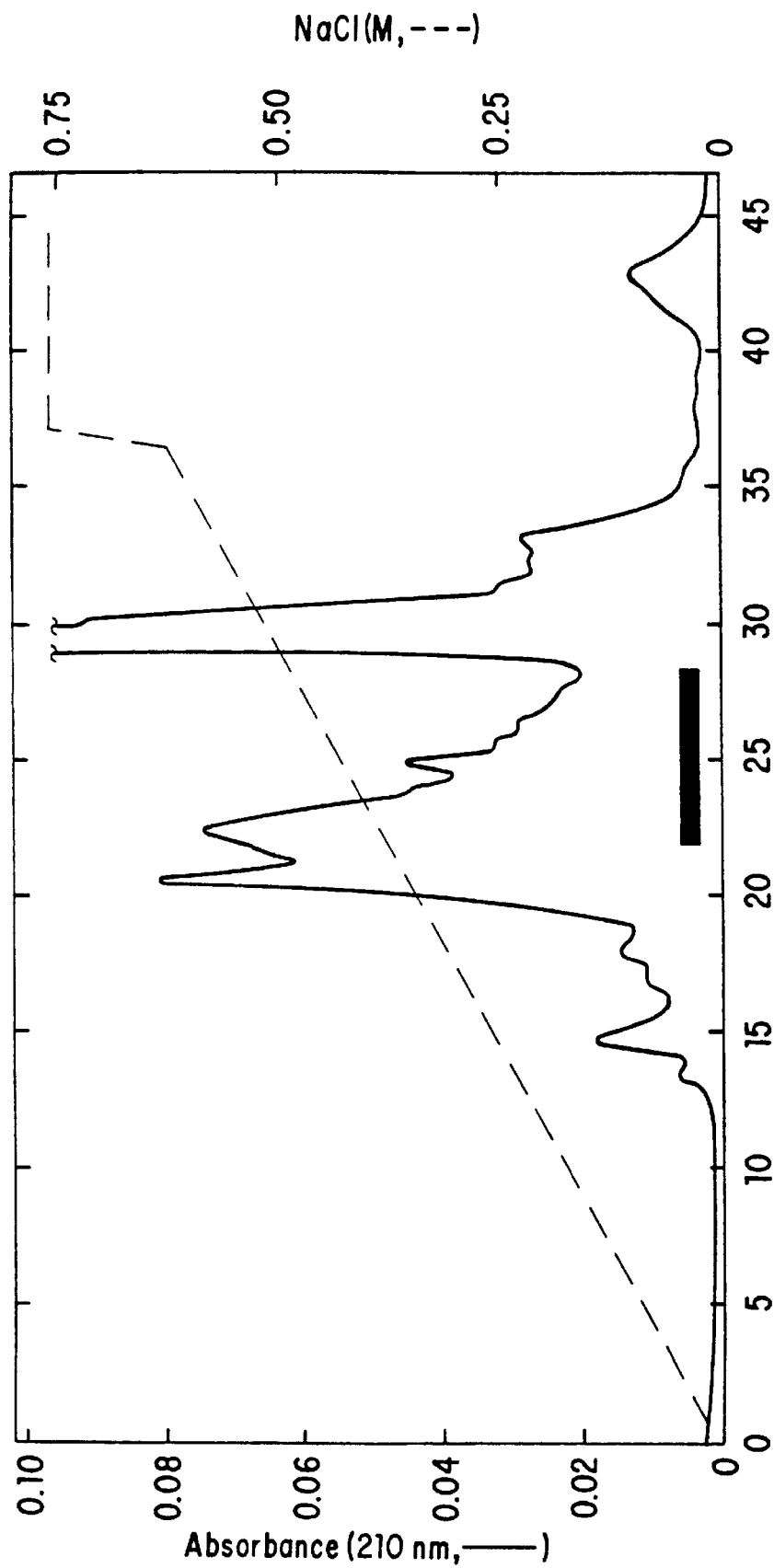
FIG. 1. VEGF II activity present in fractions eluting from a polyaspartic acid WCX HPLC cation exchange column, bar denotes pooled active fractions.

The present invention relates to a unique vascular endothelial cell growth factor (designated VEGF II), isolated and purified from glioma cell conditioned medium, which exhibits mitogenic stimulation of vascular endothelial cells. Glioma is defined herein as any neoplasm derived from one of the various types of cells that form the interstitial tissue of the central nervous system including brain, spinal cord, posterior pituitary gland and retina. Consequently, the scope of the present invention is intended to include the unique growth factor isolated and purified from any mammalian glioma tissue or other cells including cell lines. Cell lines include, but are not limited to, glioma-derived cell lines such as C6, hs 683 and GS-9L; glioblastomas such as A-172 and T98G; neuroblastomas such as IMR-32 and SK-N-MC; neurogliomas such as H4; tetromas such as XB-2; astrocytomas such as U-87 MG and U-373 MG; embryonal carcinomas and non-transformed glial or astrocyte cell lines, and the human medulloblastoma line TE 671, with GS-9L and TE 671 being preferred. VEGF II is present and can be isolated from rat tissue including ovary, heart and kidney. Anterior pituitary tumor cell lines such as GH3 and Hs 199 may also be used. Although the VEGF of this invention is described as being isolated from rat cells, the same or substantially similar growth factor may be isolated from other mammalian cells, including human cells.

Vascular endothelial growth factor II may exist in various microheterogeneous forms which are isolated from one or more of the various cells or tissues described above. Microheterogeneous forms as used herein refer to a single gene product, that is a peptide produced from a single gene unit of DNA, which is structurally modified at the mRNA level or following translation. Peptide and protein are used interchangeably herein. The microheterogeneous forms will all have equivalent mitogenic activities. Biological activity and biologically active are used interchangeably and are herein defined as the ability of VEGF II to stimulate DNA synthesis in target cells including vascular endothelial cells as described below which results in cell proliferation. The modifications may take place either in vivo or during the isolation and purification process. In vivo modification results from, but is not limited to, proteolysis, glycosylation, phosphorylation, deamidation or acetylation at the N-terminus. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which also results in production of microheterogeneous forms. The most common modification occurring during purification is proteolysis which is generally held to a minimum by the use of protease inhibitors. Under most conditions one or more microheterogeneous forms are present following purification of native VEGF II. Native VEGF II refers to VEGF II isolated and purified from cells that produce VEGF II. Vascular endothelial growth factor II may also exist in various alternatively spliced forms which is defined herein as the production of related mRNAs by differential processing of exons. Exons are defined as those parts of the DNA sequence of a eukaryotic gene that code for the final protein product.

Glioma cells such as the rat cell line GS-9L are grown to confluence in tissue culture flasks, about 175 cm$^2$, in a cell culture medium such as Dulbecco's Modified Eagle's Medium (DMEM) supplemented with about 10% newborn calf serum (NCS). When the cells reach confluence the culture medium is removed, the cell layers are washed with Ca$^{++}$, Mg$^{++}$-free phosphate buffered saline (PBS) and are removed from the flasks by treatment with a solution of trypsin, about 0.1%, and EDTA, about 0.04%. The cells, about 1×10$^8$, are pelleted by centrifugation, resuspended in about 1500 ml of DMEM containing about 5% NCS and plated into a ten level cell factory (NUNC), 6,000 cm$^2$ surface area. The cells are incubated for about 48 to about 96 hours (hr), with 72 hr preferred, at about 37° C. in an atmosphere of about 5% CO$_2$. Following incubation the medium is removed and the cell factories are washed about 3 times with PBS. About 1500 ml of fresh culture media is added containing about a 1:2 mixture of Ham's-F12/DMEM containing about 15 mM Hepes, about 5 µg/ml insulin, about 10 µg/ml transferrin and with or without about 1.0 mg/ml bovine serum albumin. This media is replaced with fresh media after about 24 hr and collected every 48 hr thereafter. The collected conditioned media are filtered through Whatmen #1 paper to remove cell debris and stored at about −20° C.

The GS-9L conditioned medium is thawed and brought to pH 6.0 with 1 M HCl. The initial purification step consists of cation exchange chromatography using a variety of cation exchangers on a variety of matrices such as CM Sephadex C-50, Pharmacia Mono S, Zetachrom SP and Polyaspartic Acid WCX (Nest Group) with CM Sephadex C-50 (Pharmacia) being preferred. The VEGF-containing culture media is mixed with CM Sephadex C-50 at about 2 gm per about 20 L of the conditioned medium and stirred at low speed for about 24 hr at 4° C. The resin is allowed to settle and the excess liquid is removed. The resin slurry is packed into a column and the remaining culture media is removed. Unbound protein is washed from the column with 0.05 M sodium phosphate, about pH 6.0, containing 0.15 M NaCl. The VEGF II is eluted with about 0.05 M sodium phosphate, about pH 6.0, containing about 0.6 M NaCl.

The active fractions collected from the CM Sephadex C-50 column are further fractionated by lectin affinity chromatography for additional purification of VEGF II. The lectins which may bind VEGF II include, but are not limited to, lectins which specifically bind mannose residues such as concanavalin A (Con A) and lens culinaris agglutinin, lectins which bind N-acetylglucosamine such as wheat germ agglutinin, lectins that bind galactose or galactosamine and lectins which bind sialic acids, with Con A being preferred. A 0.9 cm diameter column containing about 5 ml packed volume of Con A agarose (Vector Laboratories) is washed and equilibrated with about 0.05 M sodium acetate about pH 6.0, containing about 1 mM CaCl$_2$, about 1 mM MnCl$_2$ and about 0.6 M NaCl. The unbound protein is washed from the column with equilibration buffer. The VEGF II is eluted with about 0.1 M NaCl buffer containing about 0.32 M a-methyl mannoside and about 0.28 M a-methyl glucoside.

The VEGF II active eluate from the Con A column is applied to a Polyaspartic Acid WCX cation exchange high performance liquid chromatography (HPLC) column, 4.6 mm×250 mm, pre-equilibrated in about 0.05 M sodium phosphate buffer, pH 6.0. The column is eluted with a linear gradient of about 0 to 0.75 M NaCl in the phosphate buffer over about 60 minutes (min). The flow rate is maintained at about 0.75 ml/min collecting 0.75 ml fractions. Vascular endothelial growth factor activity is present in fractions eluting between approximately 21.7 and 28.5 ml, see FIG. 1.

Figure 2:
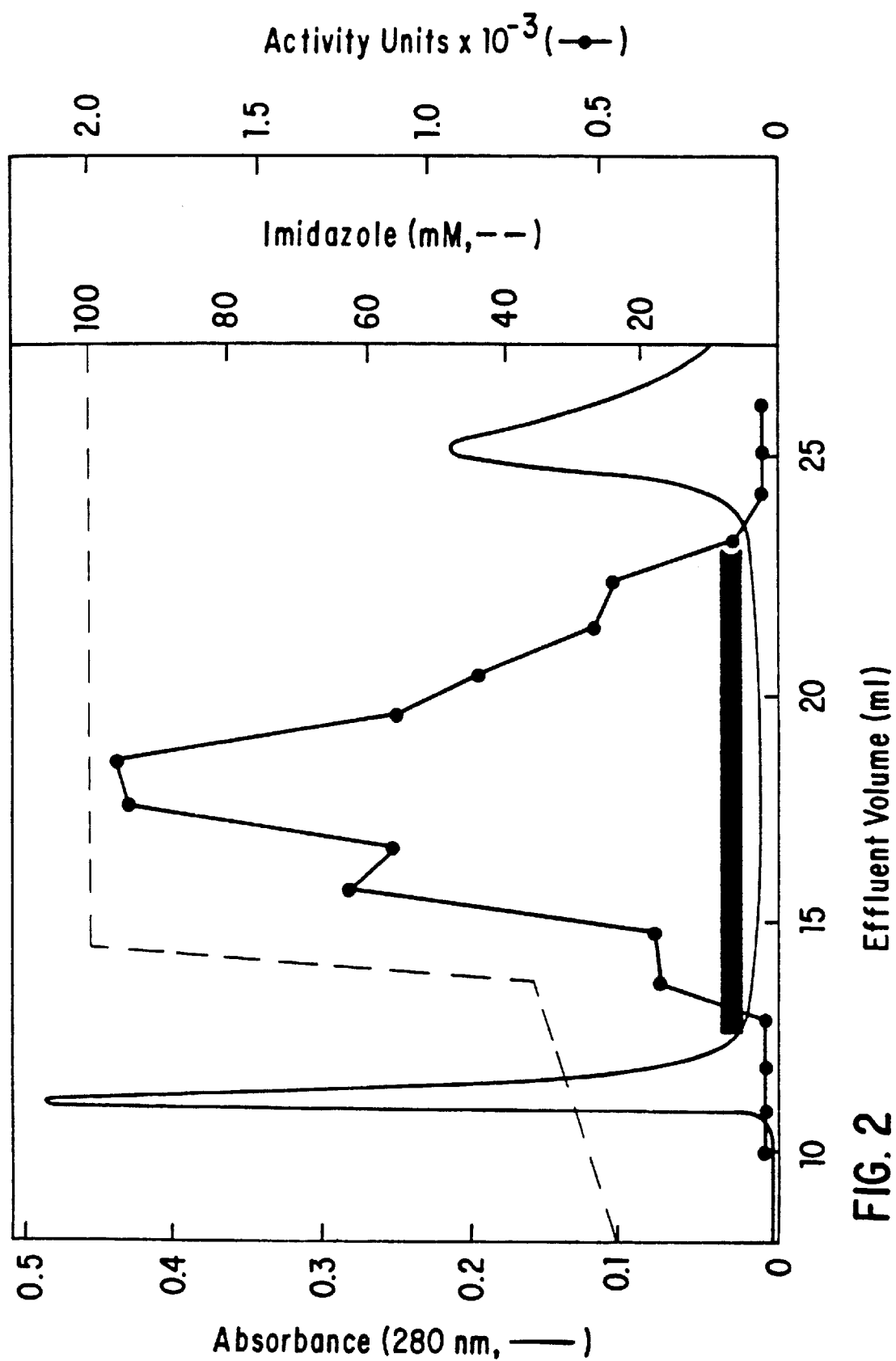
FIG. 2. VEGF II activity present in fractions eluting from a metal chelate column.

The active fractions eluted from the polyaspartic WCX column that contain VEGF II are pooled, adjusted to about pH 7.0 and loaded onto a 1×10 cm column of Pharmacia Chelating Sepharose 6B charged with an excess of copper chloride and equilibrated in about 0.05 M sodium phosphate, about pH 7.0, containing about 2 M NaCl and about 0.5 mM imidazole (A buffer). VEGF II is eluted from the column with a gradient from 0–20% B over 10 minutes, 20–35% B over 45 minutes and 35–100% B over 5 minutes at a flow rate of 0.3 ml/min, where B buffer is 0.05 M sodium phosphate, pH 7.0, containing about 2 M NaCl and 100 mM imidazole. The active fractions containing VEGF II activity eluted between about 12.6 and 22.8 ml of the gradient effluent volume, see FIG. 2.

The pooled fractions containing VEGF II activity eluted from the metal chelate column are loaded onto a 4.6 mm×5 cm Vydac C$_4$ reverse phase HPLC (RP-HPLC) column (5 µm particle size) previously equilibrated in solvent A (0.1%

Figure 3:
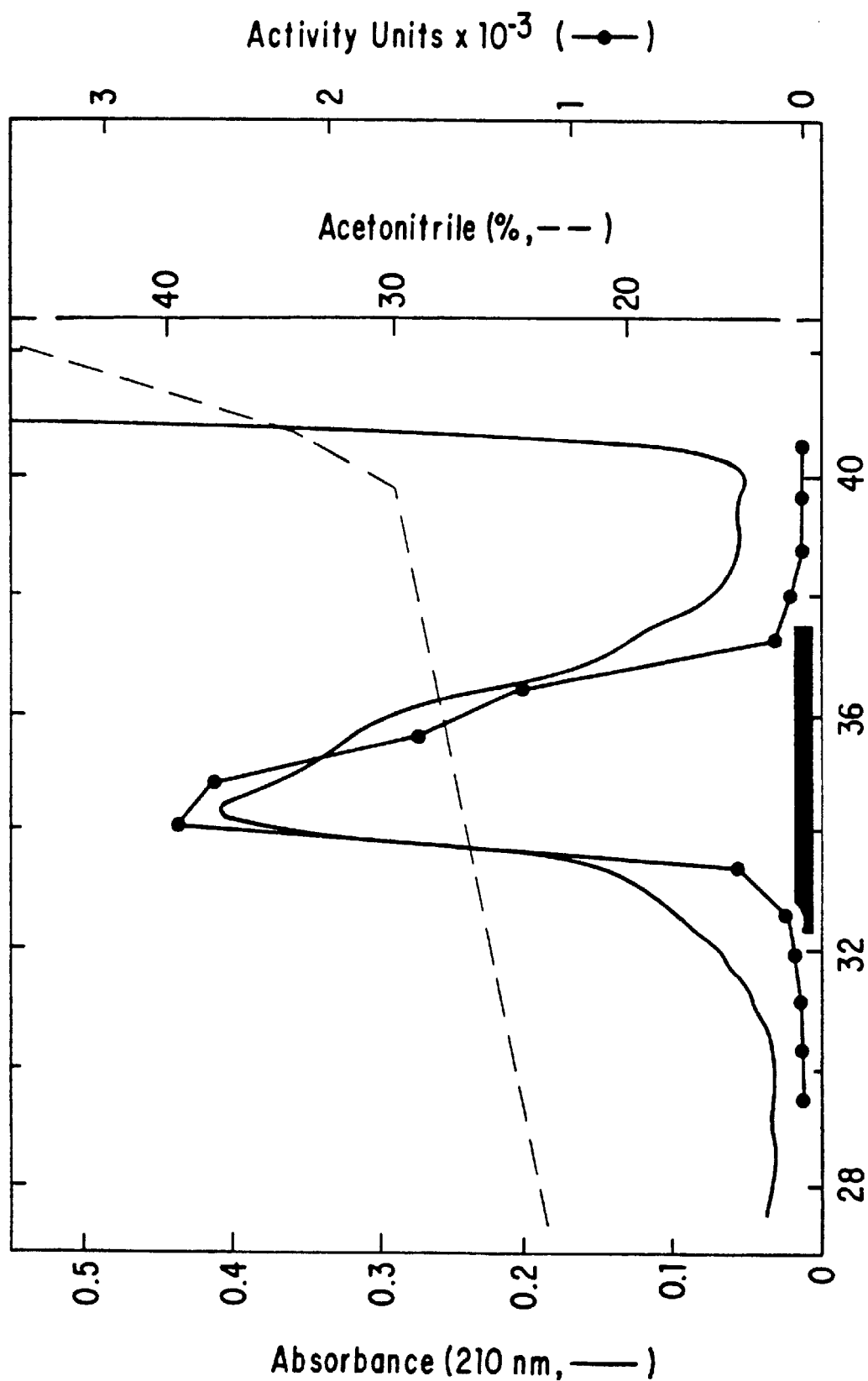
FIG. 3. VEGF II activity present in fractions eluting from a RP-HPLC $C_4$ column.

TFA). The column is eluted with a linear gradient of about 0 to 30% solvent B over 15 min, 30% B for an additional 15 min, then 30–45% B over 22.5 min and finally 45–100% B over 5.5 min. Solvent B consists of solvent A containing 67% acetonitrile (v/v). The flow rate is maintained at about 0.75 ml/min and fractions are collected every minute. The homogeneous VEGF II elutes from the $C_4$ column under these conditions at between about 32 and about 38 ml of the gradient effluent volume, see FIG. 3.

Purity of the protein is determined by sodium dodecylsulfate (SDS) polyacrylamide gel electrophoresis (PAGE) in 12.5% crosslinked gels using the technique of Laemmli, *Nature* 227: 680–684 (1970). The silver stained gels show VEGF II to consist of one band under non-reducing conditions with an approximate apparent molecular mass of about 58 kilodaltons (kDa). When a sample containing the microheterogeneous forms of VEGF II is separated under reducing conditions it migrates as two about 23 kDa subunits. The purification process results in VEGF II that is essentially free of other mammalian cell products, such as proteins. Recombinantly derived VEGF II will also be free of mammalian cell products.

Biological activity is determined by mitogenic assay using mammalian vascular endothelial cells. Human umbilical vein endothelial (HUVE) cells are plated on gelatin-coated dishes at a density of about 5000 cells per well in about 500 $\mu$l of Medium 199 (M199) containing about 20% heat-inactivated fetal calf serum (FCS). Samples to be assayed are added at the time of plating. The tissue culture plates are incubated at about 37° C. for about 12 hr and about 2 microcuries of tritiated thymidine (NEN, 20 Ci/mmol) is added per ml of assay medium (1.0 $\mu$Ci/well). The plates are incubated for a further 60 hr, the assay medium is removed and the plates are washed with Hanks balanced salt solution containing about 20 mM Hepes, about pH 7.5, and about 0.5 mg/ml bovine serum albumin. The cells are lysed and the labelled DNA solubilized with about 200 $\mu$l of a solution containing about 2 gm of sodium carbonate and about 400 mg sodium hydroxide in about 100 ml water. The incorporated radioactivity was determined by liquid scintillation counting. The concentration of VEGF which elicited a half-maximal mitogenic response in HUVE cells was approximately 2±1 ng/ml. The glycosaminoglycan heparin, which is required in these assays at a level of 10–100 $\mu$g/ml to promote a response to a positive control, acidic fibroblast growth factor, does not enhance mitogenic stimulation of these cells by VEGF II.

A purified about 1–2 $\mu$g sample of VEGF II is reduced in about 0.1 M Tris, about pH 9.5, with about 0.1% EDTA, about 6 M guanidinium chloride and about 20 mM dithiothreitol (DTT) for about 2 hr at about 50° C. The reduced protein is carboxymethylated for about 1 hr in a solution containing about 9.2 $\mu$M of unlabelled iodoacetic acid and 2.8 $\mu$M of $^{14}$C-iodoacetic acid in about 0.7 M Tris, about pH 7.8, and about 0.1% EDTA and about 6 M guanidinium chloride. The protein is carboxymethylated for about 1 hr at room temperature. The protein is isolated after reduction and carboxymethylation by RP-HPLC chromatography on a Vydac $C_4$ column, about 4.6 mm×5 cm. The protein is loaded onto a column pre-equilibrated with about 0.1% TFA and eluted by a 45 ml linear gradient from about 0.1% TFA to 0.1% TFA/67% acetonitrile at a flow rate of about 0.75 ml/min. The reduced and carboxymethylated protein eluted as two peaks at approximately 25 and 28 ml with the proportion being approximately equal as determined by monitoring absorbance at 210 nm.

Samples of the reduced and carboxymethylated monomers are applied to polybrene-coated glass fiber filters and their N-terminal sequences are determined by Edman degradation in an ABI gas phase microsequencer in conjunction with an ABI 120A on line phenylthiohydantoin analyzer following the manufacturers instructions. The protein showing the peak of absorbance eluting at approximately 28 ml (A subunit or monomer) yielded an amino terminal sequence of:

Ala Pro Thr Thr Glu Gly Glu Gln Lys Ala His Glu Val Val which is identical to the monomers of VEGF I (herein denoted A momoers or subunits), Conn et al., Proc. Natl. Acad. Sci. USA 87: 2628–2632 (1990). The peak of absorbance eluting at approximately 25 ml (B monomer or subunit) yielded an N-terminal sequence of:

Ala Leu Ser Ala Gly Asn Xxx Ser Thr Glu Met Glu Val Val Pro Phe Asn Glu Val plus a nearly equal amount of a truncated form of the same sequence missing the first three amino acid residues. The missing Xxx residue corresponds to an Asn residue in the cloned cDNA, see below. Since this missing Asn occurs in a classical Asn Xxx Ser/Thr N-glycosylation sequence it is presumed to be glycosylated. The A subunit and the total of both B subunits are recovered in nearly equal amounts supporting the interpretation that the two peptides combine to form an AB heterodimer in VEGF II.

Figure 4:
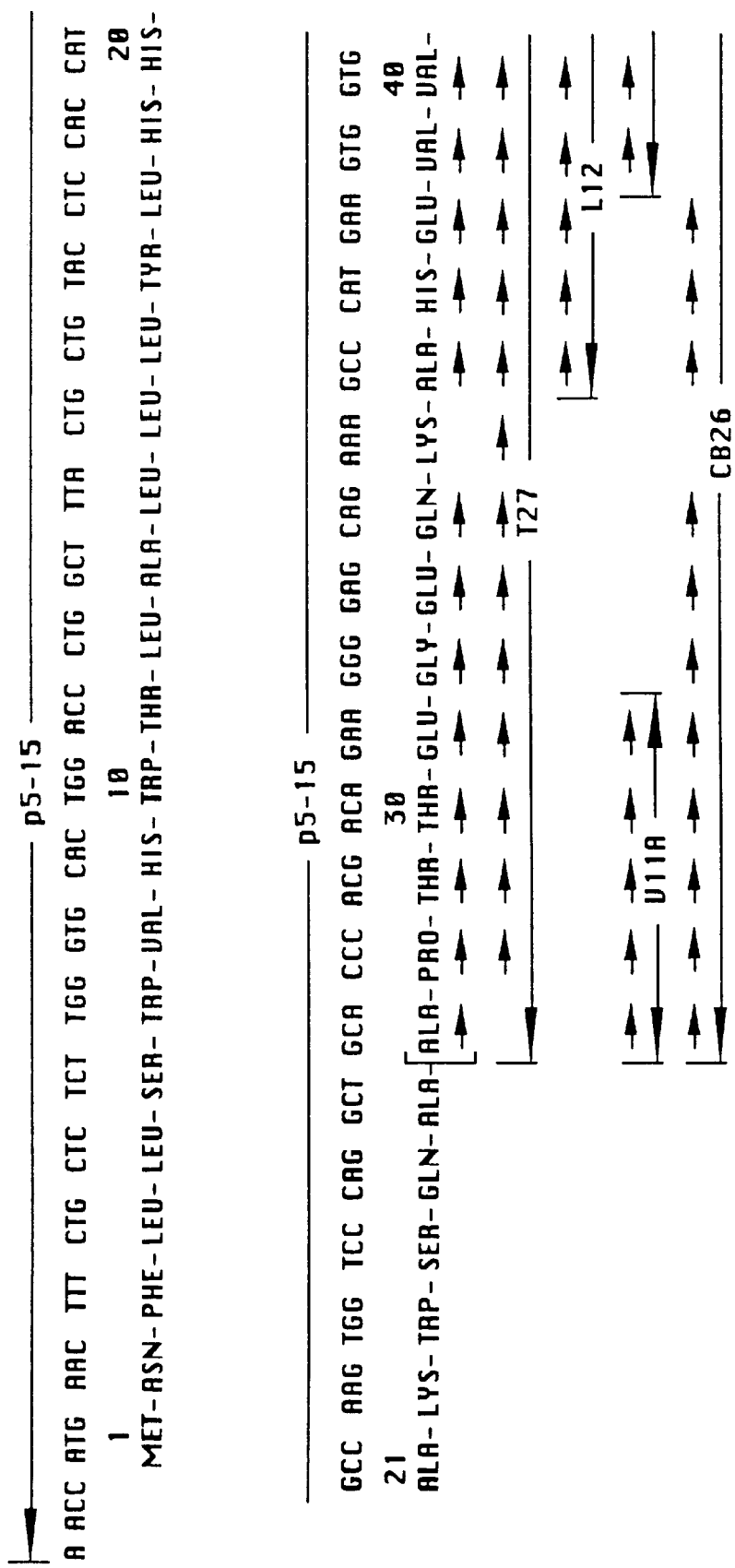
FIG. 4. Full length amino acid residue protein translation product and its cDNA coding sequence for VEGF I A subunit plus polypeptide cleavage products used to determine the amino acid sequence is shown in panels 4 through 4M.
Figure 4A:
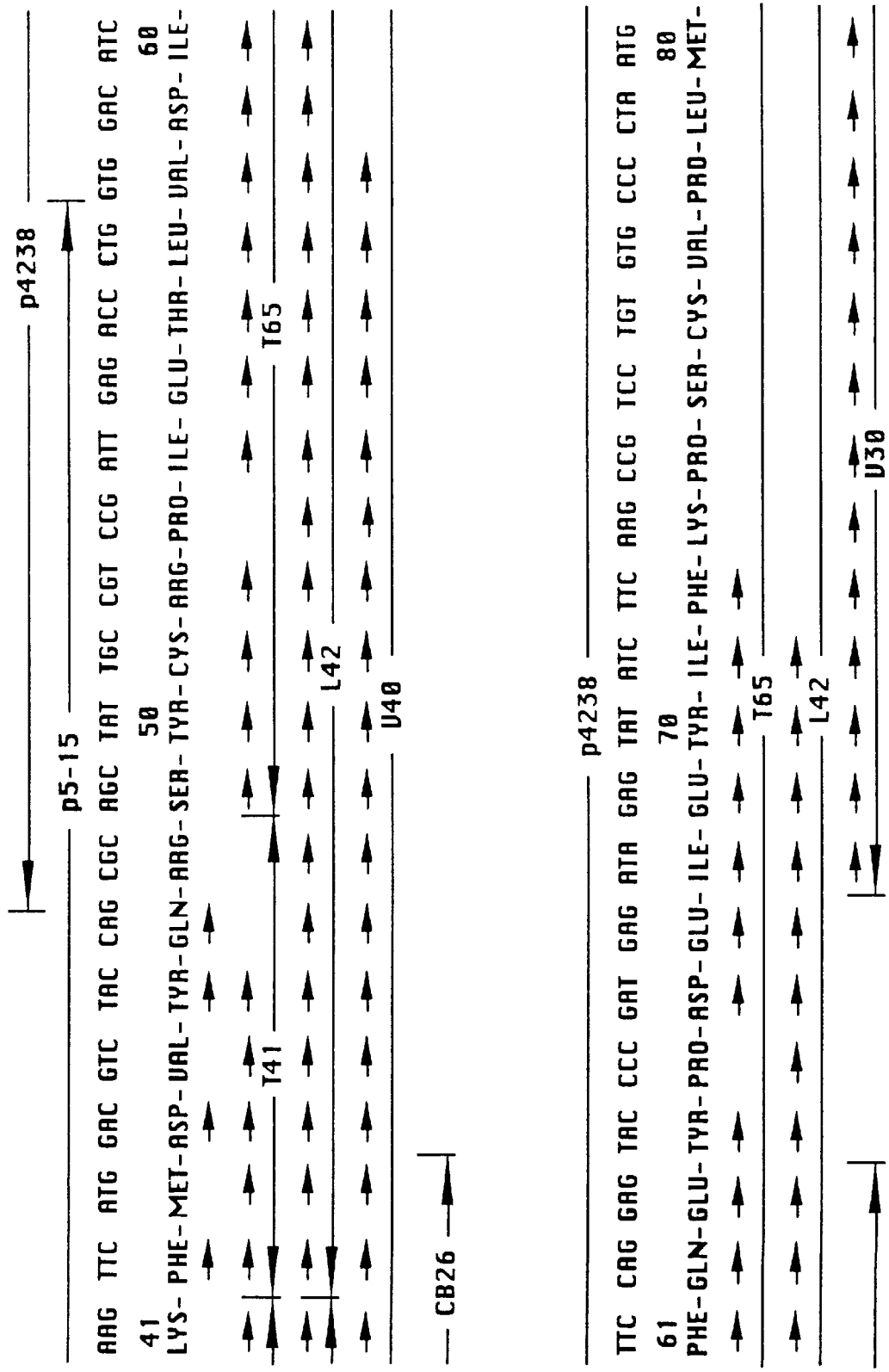
Figure 4B:
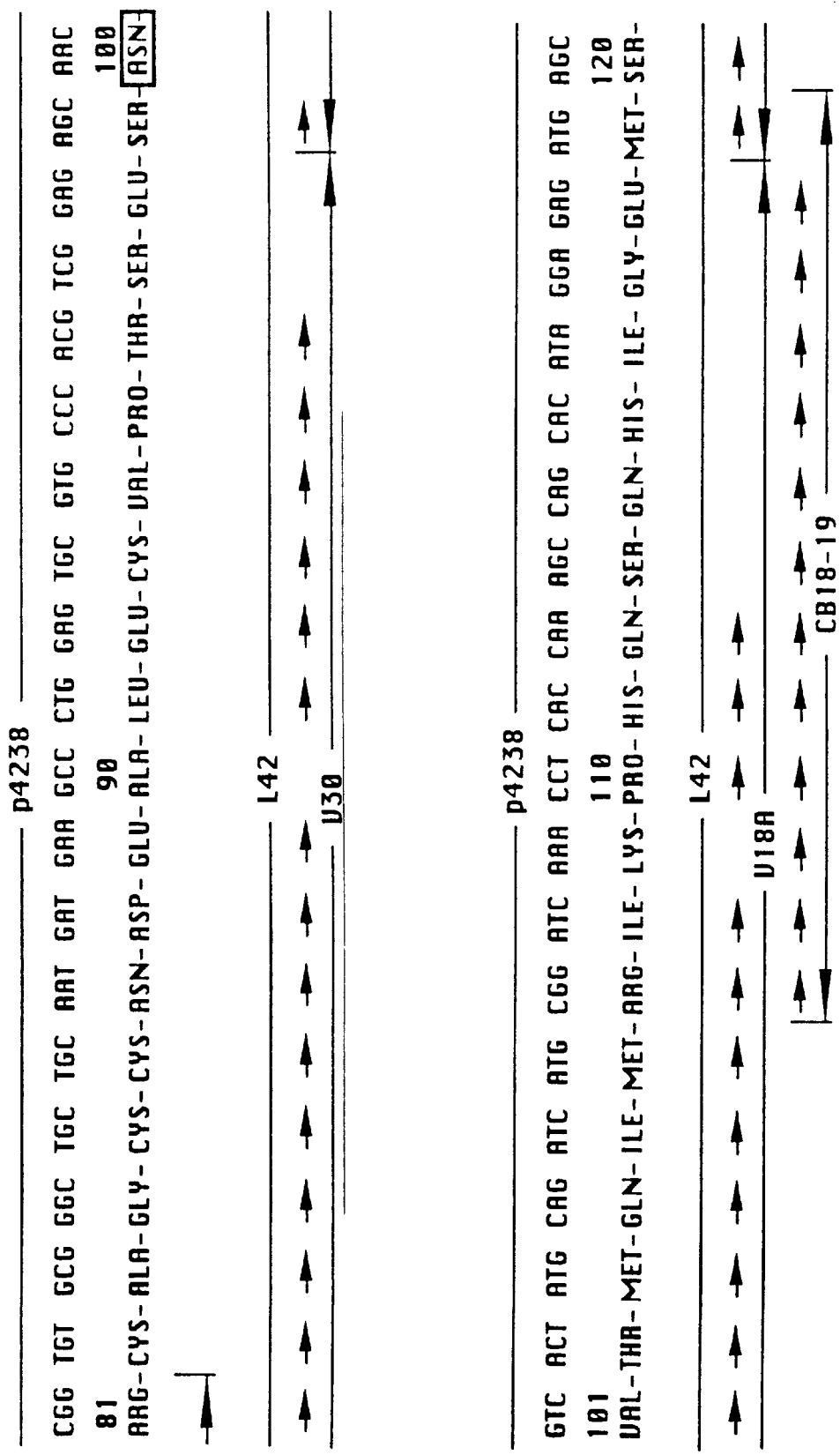
Figure 4C:
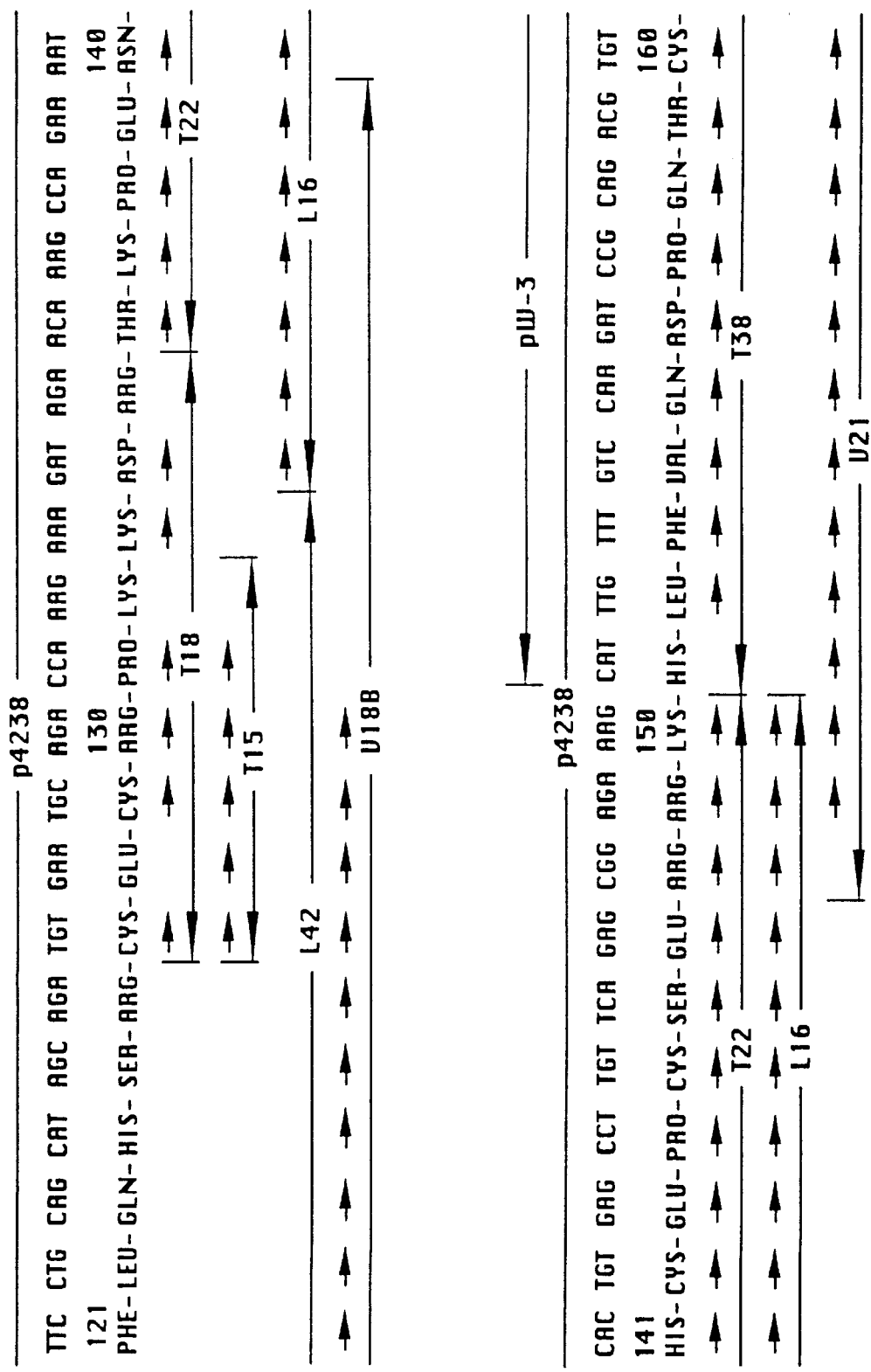
Figure 4D:
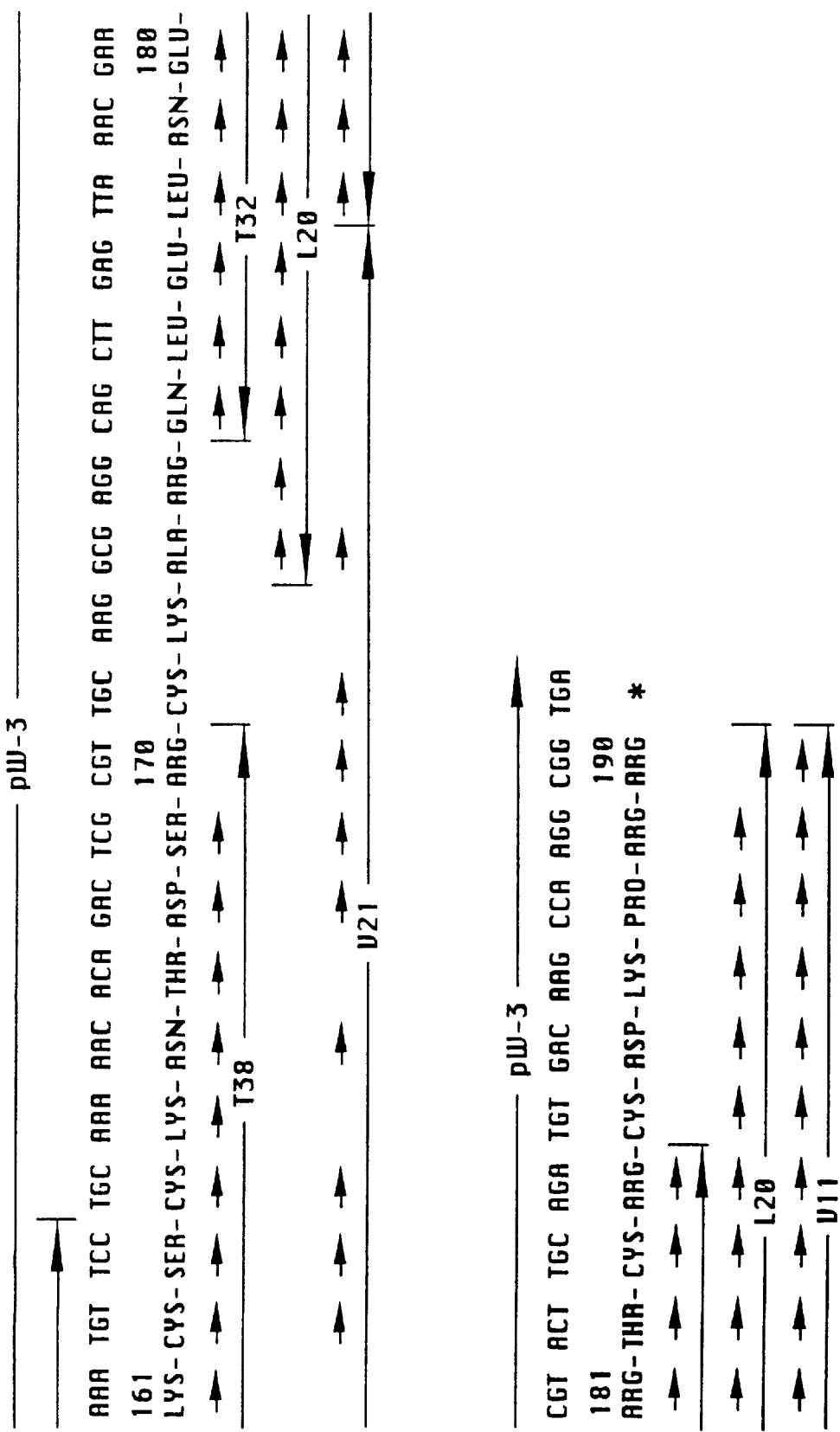
Figure 4G:
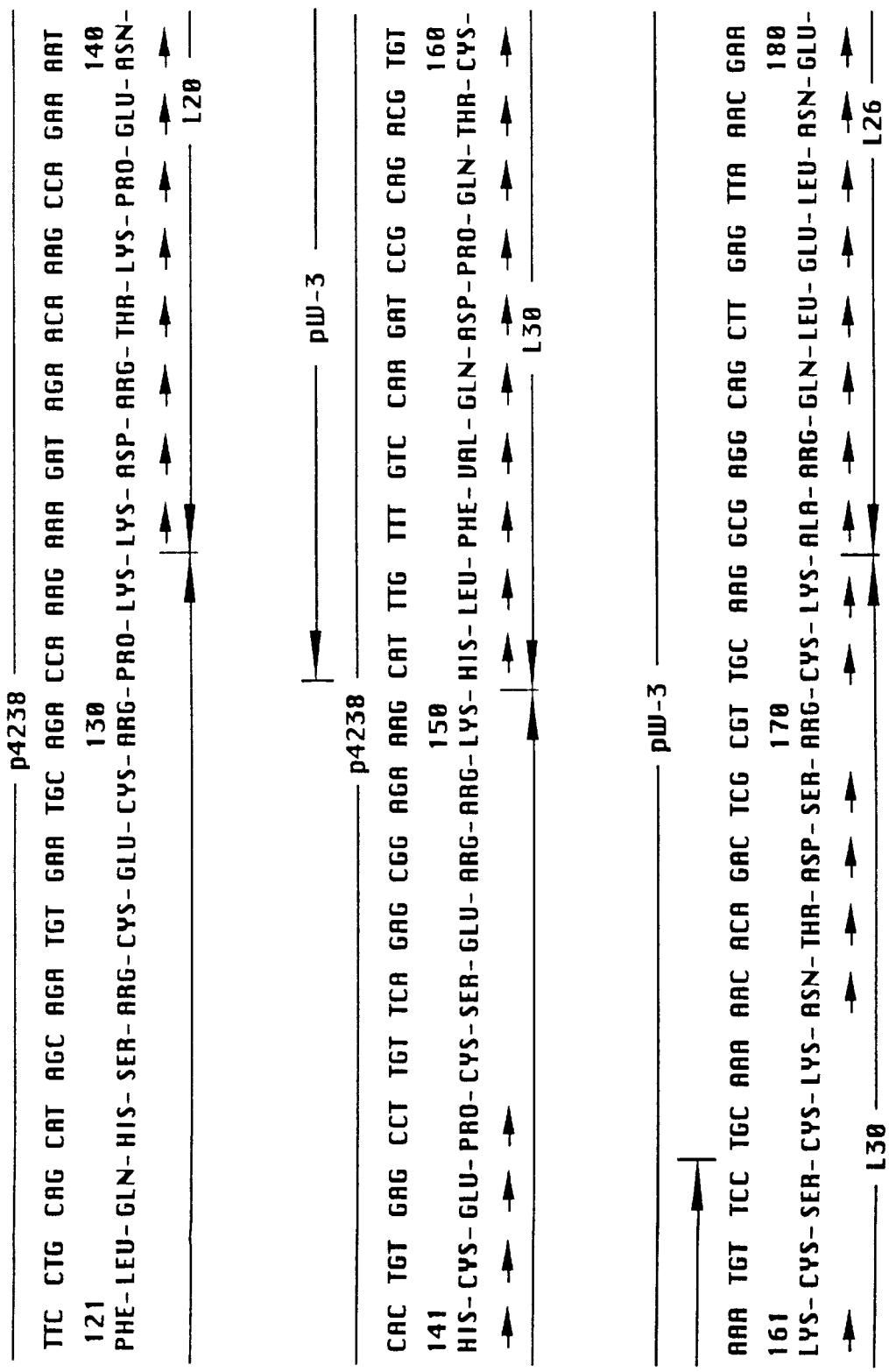
Figure 4K:
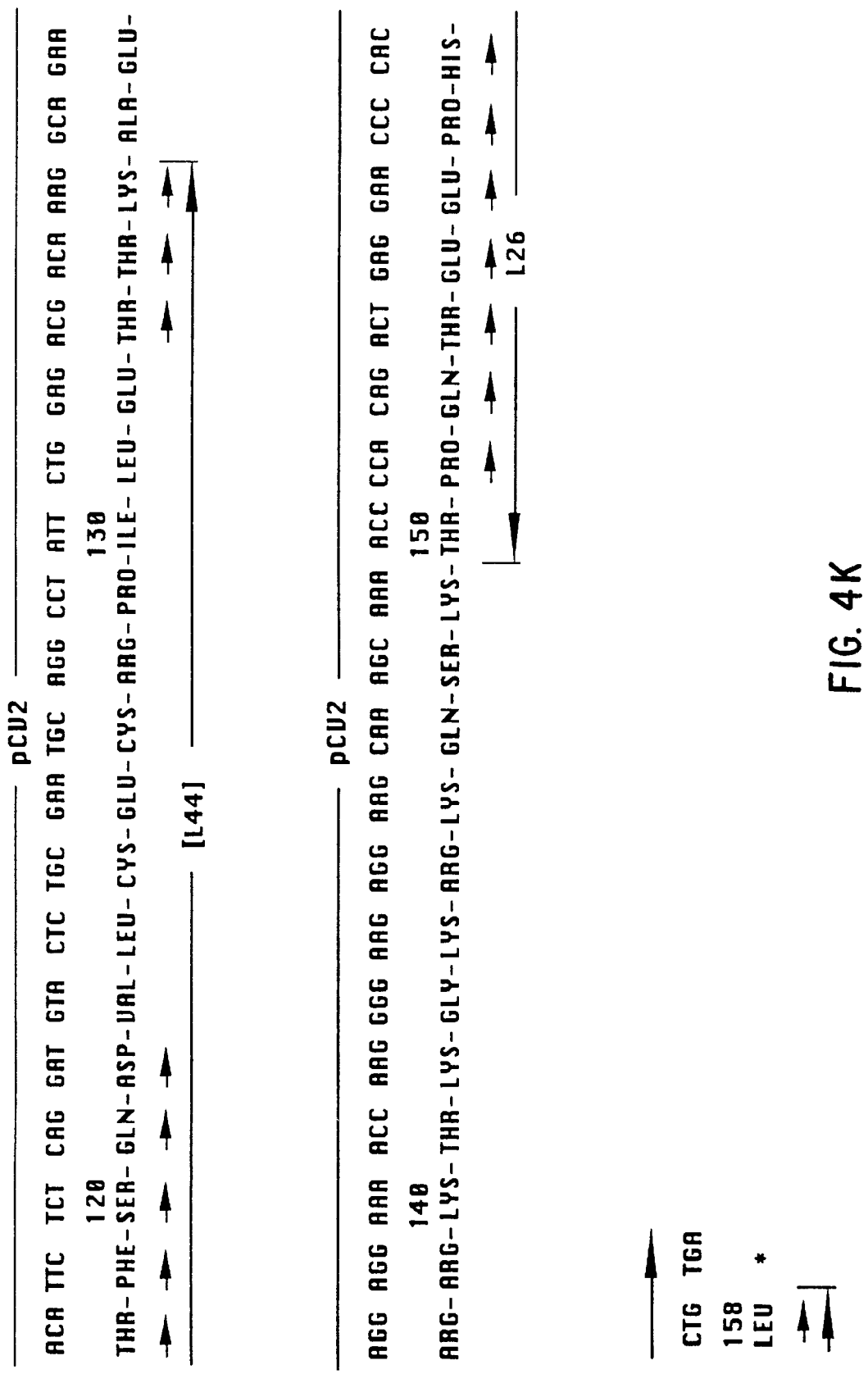

A sample of the reduced and carboxymethylated A subunit was treated with either the protease trypsin which cleaves polypeptides on the C-terminal side of lysine and arginine residues or Lys C which cleaves polypeptides on the C-terminal side of lysine by procedures well known in the art. The peptides are isolated by RP-HPLC. The amino acid sequences of the isolated peptides are determined using the Edman degradation in the ABI gas phase sequenator in conjunction with the ABI 120 A on line phenylthiohydantoin analyzer following manufacturer's instructions. The amino acid sequences are shown in FIGS. 4 through 4M.

Reduced and carboxymethylated A subunit is dried and solubilized in about 0.7 M Tris, about pH 7.8, about 6 M guanidinium chloride containing about 0.1% EDTA. V8 protease is added in 0.1 M ammonium bicarbonate buffer, about pH 8.0, and the mixture is incubated for about 48 hr at about 37° C. The protease cleaves predominantly on the carboxyl terminal side of glutamic acid residues. The resulting polypeptides were resolved by $C_{18}$ RP-HPLC as above.

The reduced and carboxymethylated A subunit protein solution is adjusted to a pH of about 6.8 with 6 N HCl and DTT is added to a final concentration of 2 M for reduction of any methionine sulfoxide to methionine residues. After about 20 hr of reduction at about 39° C. the protein is repurified by $C_4$ RP-HPLC. The product is dried and cleaved on the carboxyl terminal side of methionine residues by 200 $\mu$l of 40 mM cyanogen bromide in about 70% (v/v) formic acid under an argon atmosphere at about 20° C. for about 24 hr in the dark. The cleavage products are resolved by $C_{18}$ RP-HPLC. The amino acid sequence is shown in FIGS. 4 through 4M, see Conn et al., Proc. Natl. Acad. Sci. USA 87: 2628–2632 (1990).

The full length 190 amino acid residue protein translation product of the VEGF II A subunit, which is now known to be identical with the VEGF I A subunit, and its cDNA coding sequence are shown in FIGS. 4 through 4M and FIGS. 5 through 5C. The mature amino terminus begins at residue 27, immediately following a typical hydrophobic secretory leader sequence. A single potential N-glycosylation site exists at $Asn_{100}$. Most (143 amino acid residues) of the 164 residues of the reduced and carboxymethylated mature subunit including the amino terminus and RP-HPLC reversed phase-purified products of tryptic (T), Lys-C (L), *Staphylococcus aureus* V8 protease (V8) and cyanogen bromide (CB) cleavages, were determined by direct microsequencing (Applied Biosystems 470A) using a total of 5 µg of protein. All residues identified by amino acid sequencing are denoted by arrows pointing to the right either directly beneath the mature processed sequence following the bracket at residue 27 for the amino terminal determination of the whole subunit or, for residues identified from the polypeptide cleavage products, above the double-headed arrows spanning the length of the particular polypeptide. One listed pair of polypeptides, V18A and V18B, was sequenced as a mixture and, therefore, are only confirmatory of the cDNA-deduced amino acid sequence, see FIGS. 4 through 4M.

Samples of the reduced and carboxymethylated pure VEGF II A and B subunits were each digested with the Lys-C endoproteinase, which cleaves polypeptides on the C-terminal side of lysine residues. The peptides were isolated by RP-HPLC and their amino acid sequences were determined as described above. The locations of the peptides in the final VEGF II A and B sequences are shown in FIGS. 5 through 5C and FIGS. 6 through 6B, respectively.

The full length coding region of the A subunit is determined from three sets of overlapping cDNA clones. Degenerate oligonucleotide primers based on the amino acid sequences Phe-Met-Asp-Val-Tyr-Gln from polypeptide L42 (residues 42–47) and Cys-Lys-Asn-Thr-Asp from polypeptide T38 (residues 164–168) (see FIGS. 4 through 4M and FIGS. 5 through 5C) were used to PCR amplify the central region of the cDNA for VEGF A subunit following the procedure of Saiki et al., Science 230: 1350–1354 (1985). A single band migrating at 420 bp was gel purified, digested with SalI, ligated into pGEM3Zf(+) and sequenced. The nucleotide sequence obtained (p4238) was used to design antisense and sense PCR primers to amplify the 5' and 3' ends of the cDNA according to the protocol described by Frohman et al. Proc. Natl. Acad. Sci. USA 85: 8998–9002 (1988). These 5' and 3' clones are denoted p5–15 and pW3, respectively. Regions of complete DNA sequences, excluding the primers, determined for each set of clones are indicated by double-headed arrows above the nucleotide sequence. In addition to the cDNA coding the 164 amino acid secreted form identified by protein sequencing, two alternative cDNAs encoding a 120 amino acid and a 188 amino acid form are cloned and sequenced.

The full length coding region of the B subunit is determined from four sets of overlapping cDNA clones. Degenerate oligonucleotide primers based on the amino acid sequences from polypeptide L50 are used to PCR amplify the central region of the cDNA for VEGF II B subunit following the procedure of Saiki et al., Science 230: 1350–1354 (1985). A single band migrating at 108 bp was gel purified, digested with SalI, ligated into pGEM3Zf(+) and sequenced. The nucleotide sequence obtained (pYG) was used to design antisense and sense PCR primers to amplify the 5' and 3' ends of the cDNA according to the protocol described by Frohman et al. Proc. Natl. Acad. Sci. USA 85: 8998–9002 (1988). These 5' and 3' clones are denoted p5V2 and p3V2, respectively. Additional 5' end sequences are determined from clone 202 isolated from a cDNA library prepared from GS-9L polyA$^+$ RNA. Regions of complete DNA sequences, excluding the primers, determined for each set of clones are indicated by double-headed arrows above the nucleotide sequence. The entire base sequence for the 135 amino acid microheterogeneous B subunit and the 115 amino acid microheterogeneous B subunit are shown in FIGS. 6 through 6B and FIGS. 7 through 7A.

It is intended that vascular endothelial cell growth factor II exist as a heterodimer consisting of an A subunit and a B subunit. It is further intended that VEGF homodimers exist as either two A subunits or two B subunits. The B subunit may be either the 135 amino acid form or the 115 amino acid form. The A subunit of the may be either the 188 amino acid form, the 164 amino acid form or the 120 amino acid form. The heterodimers or heterodimer species can be depicted as: $A_{188}+B_{135}$, $A_{188}+B_{115}$, $A_{164}+B_{135}$, $A_{164}+B_{115}$, $A_{120}+B_{135}$, $A_{120}+B_{115}$, $B_{135}+B_{115}$, $A_{188}+A_{164}$, $A_{188}+A_{120}$ and $A_{164}+A_{120}$, The homodimers can be depicted as: $B_{135}+B_{135}$, $B_{115}+B_{115}$, $A_{188}+A_{188}$, and $A_{120}+A_{120}$. It is also intended that the invention include all of the individual subunit forms of both the A subunit and the B subunit of VEGF II.

It is further intended that the nucleotide sequence for vascular endothelial growth factor II be interpreted to include all codons that code for the appropriate amino acids in the sequence for each of the vascular endothelial growth factor II subunits, as indicated by the degeneracy of the genetic code. It is further intended that the nucleotide sequence and the amino acid sequence for VEGF II subunits include truncated genes or proteins which result in a protein which exhibits biological activity similar to vascular endothelial growth factor II. The scope of the invention is intended to include all naturally occurring mutations and allelic varients and any randomly generated artifical mutants which may change the sequences but do not alter biological activity as determined by the ability to stimulate the division of vascular endothelial cells.

The above described heterodimers, homodimers, subunits and monomers of vascular endothelial growth factor are characterized by being the product of chemical synthetic procedures or of procaryotic or eucaryotic host expression of the DNA sequences as described herein. A monomer is defined as a subunit that cannot form an oligomeric unit. Expression of the recombinant VEGF II genes (recombinant DNA) is accomplished by a number of different host cells which contain at least one of a number of expression vectors. Expression vectors are defined herein as DNA sequences that are required for the transcription of cloned copies of recombinant DNA sequences or genes and the translation of their mRNAs in an appropriate host. Such vectors can be used to express genes in a variety of hosts such as bacteria, blue-green algae, yeast cells, insect cells, plant cells and animal cells, with mammalian cells being preferred. The genes may also be expressed in a number of virus systems. Specifically designated vectors allow the shuttling of DNA between bacteria-yeast, bacteria-plant or bacteria-animal cells. An appropriately constructed expression vector should contain: an origin of replication for autonomous replication in host cells, selective markers, a limited number of useful restriction enzyme sites, a high copy number, and strong promoters. A promoter is defined as a DNA sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses and cosmids. The expression of mammalian genes in cultured mammalian cells is well known in the art. Sambrook et al., Molecular Cloning, A Laboratory Manual, 2nd Edition, Book 3, Cold Springs Harbor Laboratory Press (1989) and Current Protocols In Molecular Biology, Ausubel et al. Eds, Greene Publishing Associates and Wiley- Interscience, 1987 and supplements, disclose various mammalian expression vectors and vector systems along with methods for the introduction of recombinant vectors into mammalian cells. The cDNA for the monomeric forms of the A and B subunits can be expressed in a system such as that described by Linemeyer et al., European Patent Application, Publication No. 259,953. The cDNA is incorporated into a commercially available plasmid such as pKK 223-3 (Pharmacia) as modified as by Linemeyer et al. and expressed in *E. coli*. Other expression systems and host cells are well known in the art.

The high Cys content and glycoslyation of the A and B subunits along with the structure of the homo- and heterodimers suggests that expression of biologically active proteins is carried out in animal cells. Expression may be carried out in Chinese hamster ovary (CHO) cells with the cloned VEGF II DNA cotransfected with the gene encoding dihydrofolate reductase (dhfr) into dhfr- CHO cells, see Sambrook et al. Transformants expressing dhfr are selected on media lacking nucleosides and are exposed to increasing concentrations of methotrexate. The dhfr and VEGF II genes are thus coamplified leading to a stable cell line capable of expressing high levels of VEGF II. The plasmid is designed to include either an A subunit and a B subunit or two A or B subunits. The two cDNAs are operably attached so that the protein produced will be dimeric and will have VEGF II biological activity. Operably attached refers to an appropriate sequential arrangement of nucleotide segments, cDNA segments or genes such that the desired protein will be produced by cells containing an expression vector containing the operably attached genes, cDNA segments or nucleotides.

The expressed proteins (monomers or dimers) are isolated and purified by standard protein purification processes. It is to be understood that the expression vectors capable of expressing heterodimeric forms of VEGF II will contain a DNA sequence which will encode an A subunit and a DNA sequence which will encode a B subunit. Expression vectors capable of expressing homodimeric forms of VEGF will contain either one or two DNA sequences which encode either two A or two B subunits.

The ability of the various species of VEGF II to stimulate the division of vascular endothelial cells makes this protein in all microheterogeneous forms and alternative splicing forms useful as a pharmaceutical agent. The protein as used herein is intended to include all microheterogeneous forms as previously described. The protein can be used to treat wounds of mammals including humans by the administration of the novel protein to patients in need of such treatment.

The novel method for the stimulation of vascular endothelial cells comprises treating a sample of the desired vascular endothelial cells in a nutrient medium with mammalian VEGF II, preferably human or rat, at a concentration of about 1–10 ng/ml. If the vascular endothelial cell growth is conducted in vitro, the process requires the presence of a nutrient medium such as DMEM or a modification thereof and a low concentration of calf or bovine serum such as about 0 to 2% by volume. Preservatives such as antibiotics may also be included; these are well known in the art.

The novel growth factors of this invention are useful for the coverage of artificial blood vessels with vascular endothelial cells. Vascular endothelial cells from the patient would be obtained by removal of a small segment of peripheral blood vessel or capillary-containing tissue and the desired cells would be grown in culture in the presence of VEGF II and any other supplemental components that might be required for growth. After growth of adequate numbers of endothelial cells in culture to cover a synthetic polymeric blood vessel the cells would be plated on the inside surface of the vessel, such as fixed umbilical vein, which is then implanted in the patient. Alternatively, tubular supports are coated in vitro with VEGF II prior to implantation into a patient. Following implantation endothelial cells migrate into and grow on the artificial surface. Prior coating of the artificial vessel either covalently or noncovalently, with proteins such as fibrin, collagen, fibronectin or laminin would be performed to enhance attachment of the cells to the artificial surface. The cell-lined artificial vessel would then be surgically implanted into the patient and, being lined with the patients own cells, would be immunologically compatible. The non-thrombogenic endothelial cell lining should decrease the incidence of clot formation on the surface of the artificial vessel and thereby decrease the tendency of vessel blockage or embolism elsewhere.

The novel proteins are also useful for the production of artificial vessels. Vascular endothelial cells and smooth muscle cells from the patient would be obtained and grown separately in culture. The endothelial cells would be grown in the presence of VEGF II as outlined above. The smooth muscle would be grown in culture by procedures well known in the art. A tubular mesh matrix of a biocompatible polymer (either a synthetic polymer, with or without a coating of proteins, or a non-immunogenic biopolymeric material such as surgical suture thread) would be used to support the culture growth of the smooth muscle cells on the exterior side and vascular endothelial cells on the interior surface. Once the endothelial cells form a confluent monolayer on the inside surface and multiple layers of smooth muscle cells cover the outside, the vessel is implanted into the patient.

The novel peptides can also be used for the induction of tissue repair or growth. The pure VEGF II would be used to induce and promote growth of tissue by inducing vascular growth and/or repair. The peptide can be used either topically for tissue repair or intravascularly for vascular repair. For applications involving neovascularization and healing of surface wounds the formulation would be applied directly at a rate of about 10 ng to about 1 $mg/cm^2$/day. For vascular repair VEGF II is given intraveneously at a rate of about 1 $\mu$g to about 100 $\mu$g/kg/day of body weight. For internal vascular growth, the formulation would be released directly into the region to be neovascularized either from implanted slow release polymeric material or from slow release pumps or repeated injections. The release rate in either case is about 100 ng to about 100 $\mu g/day/cm^3$.

For non-topical application the VEGF is administrated in combination with pharamaceutically acceptable carriers or diluents such as phosphate buffer, saline, phosphate buffered saline, Ringer's solution, and the like, in a pharamaceutical composition according to standard pharamaceutical practice. For topical application, various pharmaceutical formulations are useful for the administration of the active compound of this invention. Such formulations include, but are not limited to, the following: ointments such as hydrophilic petrolatum or polyethylene glycol ointment; pastes which may contain gums such as xanthan gum; solutions such as alcoholic or aqueous solutions; gels such as aluminum hydroxide or sodium alginate gels; albumins such as human or animal albumins; collagens such as human or animal collagens; celluloses such as alkyl celluloses, hydroxy alkyl celluloses and alkylhydroxyalkyl celluloses, for example methylcellulose, hydroxyethyl cellulose, carboxymethyl cellulose, hydroxypropyl methylcellulose, and hydroxypropyl cellulose; polyoxamers such as Pluronic® Polyols exemplified by Pluronic® F-127; tetronics such as tetronic 1508; and alginates such as sodium alginate.

The following examples illustrate the present invention without, however, limiting the same thereto.

EXAMPLE 1

Preparation of Medium Conditioned By GS-9L Cells

GS-9L cells were grown to confluence in 175 cm$^2$ tissue culture flasks in Dulbecco's Modified Eagle's Medium/10% newborn calf serum (DMEM/NCS). At confluence the medium was decanted from the flasks, the flasks were washed with calcium and magnesium free phosphate buffered saline (PBS) and the cells were removed by treatment with a 1x solution of trypsin/EDTA. The cells (1×10$^8$) were pelleted by centrifugation, resuspended in 1500 ml of DMEM/5% NCS and plated into a ten level (6000 cm$^2$ surface area) cell factory (NUNC). After 72 hr incubation at 37° C. in a 5% $CO_2$ atmosphere the medium was decanted and the cell factories were washed 3 times with PBS. The cells were refed with 1500 ml of a 1:2 mixture of Ham's F-12/DMEM containing 25 mM Hepes, 5 µg/ml insulin, 10 µg/ml transferrin and 1.0 mg/ml bovine serum albumin. This medium was changed with fresh F-12/DMEM after 24 hr and collected every 48 hr after that. The conditioned medium was filtered through a Whatman #1 paper to remove cell debris and stored frozen at −20° C.

EXAMPLE 2

Carboxymethyl-Sephadex Chromatography

GS-9L conditioned medium, from Example 1, was thawed and brought to pH 6.0 with 1 M HCl. Two grams of CM Sephadex C-50 cation exchange (Pharmacia) resin pre-equilibrated in PBS adjusted to pH 6.0 with 1 N HCl is added to 20 liters of conditioned medium. The mixture was stirred at low speed for 24 hr at 4° C. The resin was then allowed to settle and the medium is siphoned off. The remaining resin slurry was packed into a 3.0 cm diameter column and any remaining medium is allowed to drain off. Unbound protein was washed off the column with 0.05 M sodium phosphate, pH 6.0, containing 0.15 M NaCl. Vascular endothelial growth factor activity was eluted from the column with a subsequent wash of 0.05 M sodium phosphate, pH 6.0, containing 0.6 M NaCl.

EXAMPLE 3

Concanavalin A (Con A) Lectin Affinity Chromatography

A 0.9 cm diameter column containing about 5 ml of packed Con A agarose (Vector Laboratories) was equilibrated with 0.05 M sodium acetate, pH 6.0, containing 1 mM Ca$^{++}$, 1 mM Mn$^{++}$ and 0.6 M NaCl. The active eluate from the CM Sephadex C-50 column, Example 2, was applied to the Con A agarose and unbound protein was washed from the column with equilibration buffer. The column was then rinsed with three column volumes of 0.05 M sodium acetate, pH 6.0, containing 1 mM Ca$^{++}$, 1 mM Mn$^{++}$ and 0.1 M NaCl. Bound protein was subsequently eluted from the column by application of this buffer supplemented with 0.32 M a-methyl mannoside and 0.28 M a-methyl glucoside.

EXAMPLE 4

Polyaspartic Acid WCX HPLC Cation Exchange Chromatography

The active eluate from the Con A column, Example 3, was applied to a 25 cm×4.6 mm poly(aspartic acid) WCX cation exchange HPLC column (Nest Group) pre-equilibrated in 0.05 M sodium phosphate buffer, pH 6.0. The column was eluted with a linear gradient of 0 to 0.75 M NaCl in this buffer over 60 min at a flow rate of 0.75 ml/min collecting 0.75 ml fractions. VEGF II activity present in fractions eluting between approximately 21.7 and 28.5 ml were pooled as shown by solid horizontal bar in FIG. 1.

EXAMPLE 5

Metal Chelate Chromatography

The active fractions eluted from the poly(aspartic acid) WCX column, Example 4, that contain VEGF II were pooled, adjusted to pH 7.0 and loaded onto a 1×10 cm column of Pharmacia Chelating Sepharose 6B charged with an excess of copper chloride and equilibrated in 0.05 M sodium phosphate, pH 7.0, containing 2 M NaCl and 0.5 mM imidazole (A buffer). VEGF II was eluted from the column with a gradient from 0–20% B over 10 min, 20–35% B over 45 min and 35–100% B over 5 min at a flow rate of 0.3 ml/min, where B buffer was 0.05 M sodium phosphate, pH 7.0, containing 2 M NaCl and 100 mM imidazole. The active fractions containing VEGF II activity eluting between 12.6 and 22.8 ml of the gradient effluent volume were pooled as shown by the solid horizontal bar in FIG. 2.

EXAMPLE 6

Reverse Phase Chromatography

The fractions containing VEGF II activity pooled from the metal chelate column, Example 5 were loaded onto a 4.6 mm×5 cm Vydac C$_4$ RP-HPLC column (5 µm particle size) equilibrated in solvent A (0.1% TFA). The column was eluted with a gradient of 0–30% solvent B over 15 min, 30% B for an additional 15 min, then 30–45% B over 22.5 min and finally 45–100% B over 5.5 min where solvent B=A containing 67% acetonitrile. The flow rate was maintained at 0.75 ml/min. The active VEGF II fractions eluting between approximately 32.2 and 37.5 ml of the gradient effluent volume were pooled as shown by the solid horizontal bar in FIG. 3.

EXAMPLE 7

Mitogenic Assays

Human umbilical vein endothelial cells (HUVE) were plated on gelatin-coated 48 well tissue culture dishes at a density of 5000 cells/well in 500 µl of Medium 199 containing 20% heat inactivated fetal calf serum (FCS). Samples to be assayed were added at the time of plating. The tissue culture plates are incubated at 37° C. for 12 hr and 2 microcuries of tritiated thymidine (NEN, 20 Ci/mmol) were added per ml of assay medium (1.0 µCi/well). The plates were incubated for a further 60 hr, the assay medium was removed and the plates were washed with Hanks balanced salt solution containing 20 mM Hepes, pH 7.5, and 0.5 mg/ml bovine serum albumin. The cells were lysed and the labelled DNA solubilized with 200 µl of a solution containing 2 gm of sodium carbonate and 400 mg sodium hydroxide in 100 ml water. The incorporated radioactivity was determined by liquid scintillation counting.

The concentration of VEGF II which elicited a half-maximal mitogenic response in HUVE cells was approximately 2±1 ng/ml. The glycosaminoglycan heparin, which is required in these assays at a level of 10–100 µg/ml to promote a response to a positive control, acidic fibroblast growth factor, does not enhance mitogenic stimulation of these cells by VEGF II.

EXAMPLE 8

Purity and Protein Structure Characterization of VEGF II

Purity of the protein under non-reducing conditions was determined by SDS-PAGE in 12.5% crosslinked gels according to the method of Laemmli, Nature 227:680–685 (1970). The silver-stained gel contained a single band with an apparent mass of approximately 58 kDa. VEGF II migrated in SDS-PAGE under reducing conditions in 15% crosslinked gels as a broad silver-stained band with apparent molecular mass of approximately 23 kDa.

VEGF II was stored a 4° C. in the aqueous TFA/acetonitrile mixture used to elute the homogeneous protein in $C_4$ RP-HPLC chromatography at the final stage of the purification protocol previously described. Aliquots of the purified protein (1–2 μg) were vacuum evaporated to dryness in acid-washed 10×75 mm glass tubes and reduced for 2 hr at 50° C. in 100 μl of 0.1 M Tris buffer, pH 9.5, and 6 M guanidinium chloride containing 0.1% EDTA and 20 mM DTT (Calbiochem, Ultrol grade) under an argon atmosphere. The reduced protein was subsequently carboxymethylated for 1 hr at 20° C. by the addition of 100 μl of 0.7 M Tris, pH 7.8, containing 0.1% EDTA, 6 M guanidinium chloride, 9.2 μM unlabeled iodoacetic acid and 50 μCi of iodo[2-$^{14}$C]acetic acid (17.9 mCi/mmole, Amersham). After completion of the carboxymethylation, the mixture was loaded directly onto a 4.6 mm×5.0 cm Vydac $C_4$ column which had been preequilibrated in 0.1% TFA. The reduced and carboxymethylated protein was repurified by elution with a 45 min linear gradient of 0 to 67% (v/v) acetonitrile in 0.1% TFA at a flow rate of 0.75 ml/min and stored in this elution solution at 4° C. The reduced and carboxymethylated protein eluted as two peaks at approximately 25 and 28 ml that were of approximately equal area as determined by monitoring absorbance at 210 nm.

Samples of the two protein subunits isolated after reduction and carboxymethylation were each applied to polybrene-coated glass fiber filters and their N-terminal sequences were determined by Edman degradation in an ABI gas phase microsequencer in conjunction with an ABI 120A on line phenylthiohydantoin analyzer following manufacturers instructions. The peak of absorbance eluting at approximately 28 ml (A subunit) yielded an amino terminal sequence APTTEGEQKAHEVV identical to VEGF I. The peak of absorbance eluting at approximately 25 ml (B subunit) yielded the N-terminal sequence ALSAGN(X)STEMEVVPFNEV plus a nearly equal amount of a truncated form of the same sequence missing the first three residues. The missing X residue corresponds to an Asn in the cloned sequence. Since this missing Asn occurs in a classical Asn-X-Ser/Thr N-glycosylation sequence it is presumed to be glycosylated. The A and sum of the B chain peptides were recovered in nearly equal amounts supporting the interpretation that the two peptides combine to form an AB heterodimer in VEGF II.

Reduced and carboxymethylated A and B subunits (650 ng each) were each dried by vacuum evaporation in acid-washed 10×75 mm glass tubes. Lys C protease (50 ng, Boehringer Mannheim), an enzyme that cleaves on the carboxyl terminal side of lysine residues, was added to each tube in 100 μl of 25 mM Tris, pH 8.5, 0.1% EDTA. The substrate protein subunits were separately digested at 37° C. for 8 hr and the resulting polypeptides resolved by RP-HPLC chromatography on a 4.6 mm×25 cm Vydac $C_{18}$ column equilibrated in 0.1% TFA. Polypeptides were fractionated by elution with a 2 hr linear gradient of 0–67% acetonitrile in 0.1% TFA at a flow rate of 0.75 ml/min at 20° C. Individual peaks were manually collected and stored in this elution solution at 4° C.

The amino acid sequences of the isolated peptides were then determined using Edman degradation in an ABI gas phase sequenator in conjunction with the ABI 120 A on line phenylthiohydantoin analyzer (Applied Biosystems Int.). The peptide sequences are shown in the following FIGS. 5 through 5C and FIGS. 6 through 6B. The amino acid sequence of Lys C fragment L20 (FIGS. 5 through 5C) demonstrates that the form of VEGF II A subunit in the heterodimer is the 164 amino acid form. The amino acid sequence of Lyc C fragment L26 (FIGS. 6 through 6B) demonstrates that the form of VEGF II B subunit in the heterodimer is the 135 amino acid form.

EXAMPLE 9

Cloning and Sequencing of the VEGF II A Monomer

PCR Amplification, Cloning and Sequencing of P4238

Two degenerate oligonucleotides were synthesized in order to amplify the cDNA encoding the peptide sequences of VEGF A subunit between LysC fragment L 42 and tryptic fragment T38. These oligonucleotides were:

L42.2
  5'TTTGTCGACTT[TC]ATGGA[TC]GT[N]TA[TC]CA 3'
T383'B
  5'CAGAGAATTCGTCGACA[AG]TC[N]GT[AG]TT[TC]TT[AG]CA 3' where N=ACGT.

Poly A⁺ RNA was isolated from GS-9L cells using the Fast Track RNA isolation kit from Invitrogen and the protocol provided. First strand cDNA synthesis was performed as follows:

1 μg of GS-9L RNA was annealled to 1 μg of adapter primer TA17 5'GACTCGAGTCGACATCGATTTTTTTTTTTTTTTTT 3', by incubating in a volume of 10 μl at 70° C. for 5 min. followed by cooling to room temperature. To this reaction was added:

3.0 μl water
2.5 μl 10× buffer (500 mM Tris-HCl, pH 8.3, 750 mM KCl, 100 mM $MgCl_2$, 5 mM spermidine)
2.5 μl 100 mM DTT
2.5 μl 10 mM each dATP, dGTP, dCTP, dTTP
0.6 μl 15 units RNasin
2.5 μl 40 mM Na pyrophosphate
1.5 μl 15 units reverse transcriptase
and the reaction was incubated at 42° C. for 1 hr, then diluted to 1 ml in 10 mM Tris-HCl 1 mM EDTA, pH 7.5.
PCR Reactions
Primary reaction (100 μl)
10 μl 10× buffer from Perkin Elmer Cetus GeneAmp kit
16 μl 1.25 mM each stock of dATP, dCTP, dGTP, and dTTP
2 μl first strand GS9L cDNA
2 μl 50 pMoles L42.2
2 μl 50 pMoles T383'B
0.5 μl 2.5 units Amplitaq DNA polymerase
67.5 μl water Reaction conditions, 40 cycles of 94° C., 1'; 50° C., 2'30"; 72° C., 2'.
Prep scale secondary reaction:
100 µl 10× buffer
160 µl 1.25 mM each stock of dATP, dCTP, dGTP, and dTTP
10 µl primary PCR reaction
20 µl 500 pMoles L42.2
20 µl 500 pMoles T383'B
5 µl 25 units Amplitaq DNA polymerase
685 µwater
Reaction conditions 94° C., 1'; 55° C., 2'; 72° C., 2'; 30 cycles.

The PCR product was concentrated by Centricon 30 spin columns, purified on a 1% agarose gel, and digested with restriction endonuclease SalI. The SalI fragment was then ligated into SalI cut pGEM3Zf(+). The ligation mix was used to transform *E. coli* XL-1 blue. Plasmid DNA was isolated from white transformants and sequenced by the dideoxy chain termination method.

PCR Amplification, Cloning and Sequencing of pW-3
Based on the sequence obtained from the p4238 clones, two specific PCR primers were synthesized;
oligo 307
5' TTTGTCGACTCAGAGCGGAGAAAGC 3' and
oligo 289
5' TTTGTCGACGAAAATCACTGTGAGC 3'.
These primers were used in combination with
oligoA 17
5' GACTCGAGTCGACATCG 3'
to amplify the cDNA encoding the COOH terminus of VEGF A subunit using the 3' RACE technique described by Frohman et al., Proc. Natl. Acad. Sci. 85:8998–9002 (1988).
PCR Reactions
Primary reaction 100 µl
10 µl 10× buffer from Perkin Elmer Cetus GeneAmp kit
18 µl 1.25 mM each stock of dATP, dCTP, dGTP, and dTTP
0.35 µl first strand GS-9L cDNA
2 µl 50 pMoles oligo 289
0.5 µl 2.5 units Amplitaq DNA polymerase
67.15 µl water
Reaction conditions 94° C., 1'; 58° C., 2'; 72° C., 2'; 10 cycles then add 50 pMoles A17, then 1 cycle of 94° C., 1'; 58° C., 2'; 72° C., 40' followed by 40 cycles 94° C., 1'; 58° C., 2'; 72° C., 2'.
Prep Scale secondary reaction:
60 µl 10× buffer
108 µl 1.25 mM each stock of dATP, dCTP, dGTP, and dTTP
24 µl primary PCR reaction
12 µl 300 pMoles oligo 307
12 µl 300 pMoles oligo A17
3 µl 15 units Amplitaq DNA polymerase
381 µl water
Reaction conditions 94° C., 1'; 58° C., 2'; 72° C., 2'; 30 cycles.

The PCR product was purified on a 1% agarose gel and digested with restriction endonuclease SalI. The SalI fragment was then ligated into SalI cut pGEM3Zf(+). The ligation mix was used to transform *E. coli* XL-1 blue. Plasmid DNA was isolated from white transformants and sequenced by the dideoxy chain termination method.

PCR Amplification, Cloning and Sequencing of p5–15
Based on the sequence of p4238 clones, two specific PCR primers were synthesized;
oligo 113
5' TTTGTCGACAACACAGGACGGCTTGAAG 3'
and oligo 74
5' TTTGTCGACATACTCCTGGAAGATGTCC 3'.
These primers were used in combination with
oligo A17
5' GACTCGAGTCGACATCG 3'
to amplify the cDNA encoding the amino terminus of VEGF A subunit using the 5' RACE technique described by Frohman et al., supra. Oligo 151 was synthesized in order to specifically prime VEGF A subunit cDNA from GS-9L RNA.
Oligo 151 is:
5' CTTCATCATTGCAGCAGC 3'.

RNA was isolated from GS-9L cells using the Fast Track RNA isolation kit from Invitrogen using the protocol provided. First strand cDNA synthesis was performed as follows;

One µg of GS9L RNA was annealled to 1 µg of oligo 151 by incubating in a volume of 6 µl at 70° C. for 5' followed by cooling to room temperature. To this reaction was added:
1.5 µl 10× buffer (500 mM Tris-HCl, pH 8.3, 750 mM KCl, 100 mM MgCl$_2$, 5 mM spermidine)
2.5 µl 10 mM DTT
2.5 µl 10 mM each dATP, dGTP, dCTP, dTTP 0.6 µl 25 units RNasin
2.5 µl 40 mM Na pyrophosphate
9.5 µl 20 units diluted reverse transcriptase
The reaction was incubated at 42° C. for 1 hour.
Excess oligo151 was removed by Centricon 100 spin columns and the 5' end of the cDNA was tailed by the addition of dATP and terminal transferase. The tailed cDNA was diluted to a final volume of 150 µl in 10 mM Tris-HCl, 1 mM EDTA, pH 7.5.
PCR Reactions
Primary reaction (50 µl)
5 µl 10× buffer from Perkin Elmer Cetus GeneAmp Kit
8 µl 1.25 mM each stock of dATP,dCTP,dGTP, and dTTP
5 µl first strand GS-9L cDNA prime with oligo 151 and tailed
1 µl 25 pmoles oligo 113
1 µl 25 pMoles oligo A17
1 µl 10 pMoles oligo TA17
0.25 µl 1.25 units Amplitq DNA polymersase
28.75 µl water
Reaction conditions; 1 cycle 94° C. 1'; 50° C. 2'; 72° C. 40' then 40 cycles of 94° C. 1'; 50° C. 1'30"; 72° C. 2'
Prep scale secondary reaction:
60 µl 10× buffer
96 µl 1.25 mM each stock of dATP, dCTP, dGTP, and dTTP
6 µl primary PCR reaction
12 µl 300 pMoles oligo74
12 µl 300 pMoles oligo A17
3 µl 15 units Amplitaq DNA polymerase
411 µl water
Reaction conditions 94° C., 1'; 55° C., 2'; 72° C., 2' 30 cycles.

The PCR product was concentrated by Centricon 100 spin columns, and digested with restriction endonuclease SalI.

Figure 5:
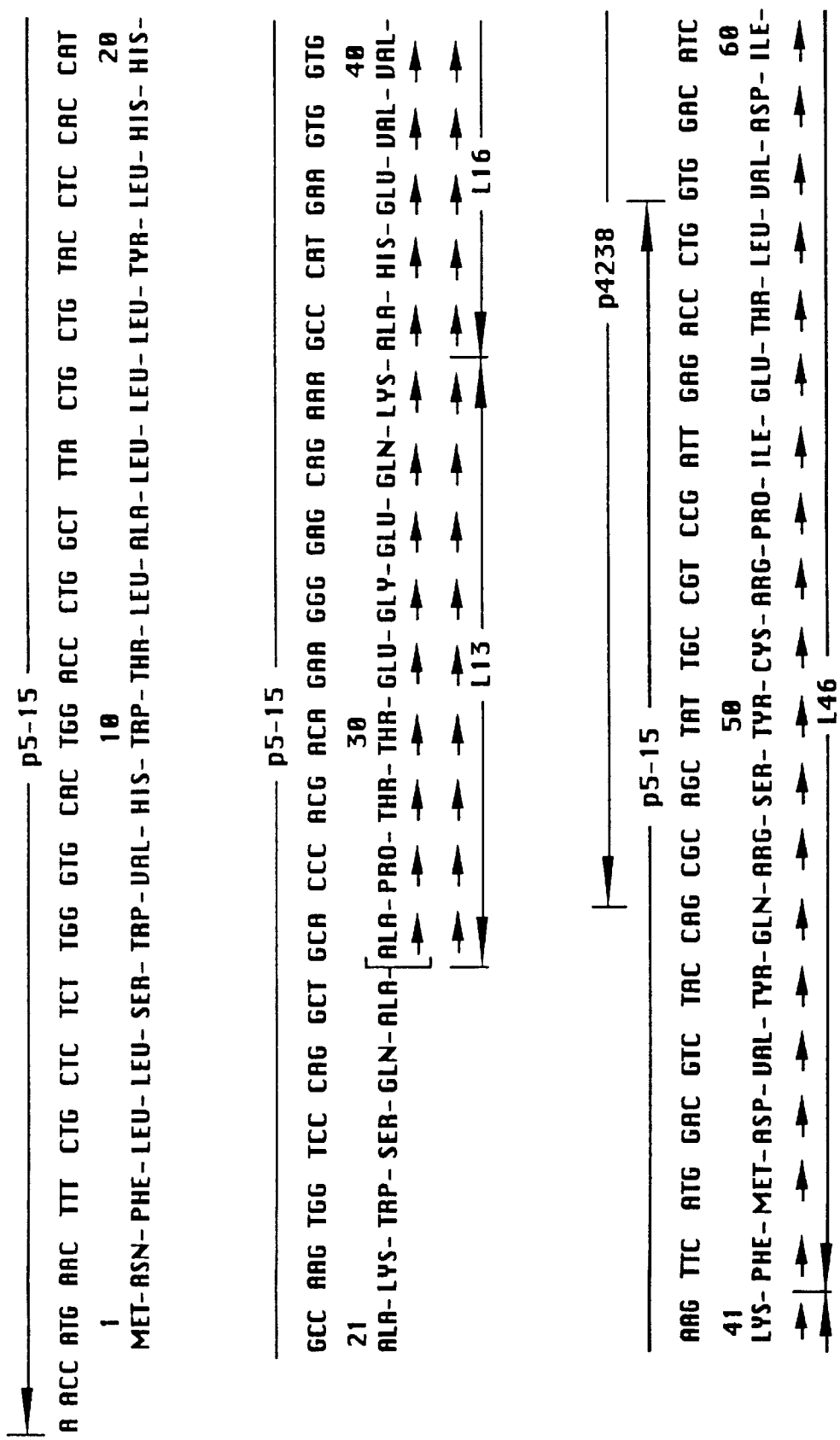
Figure 5B:
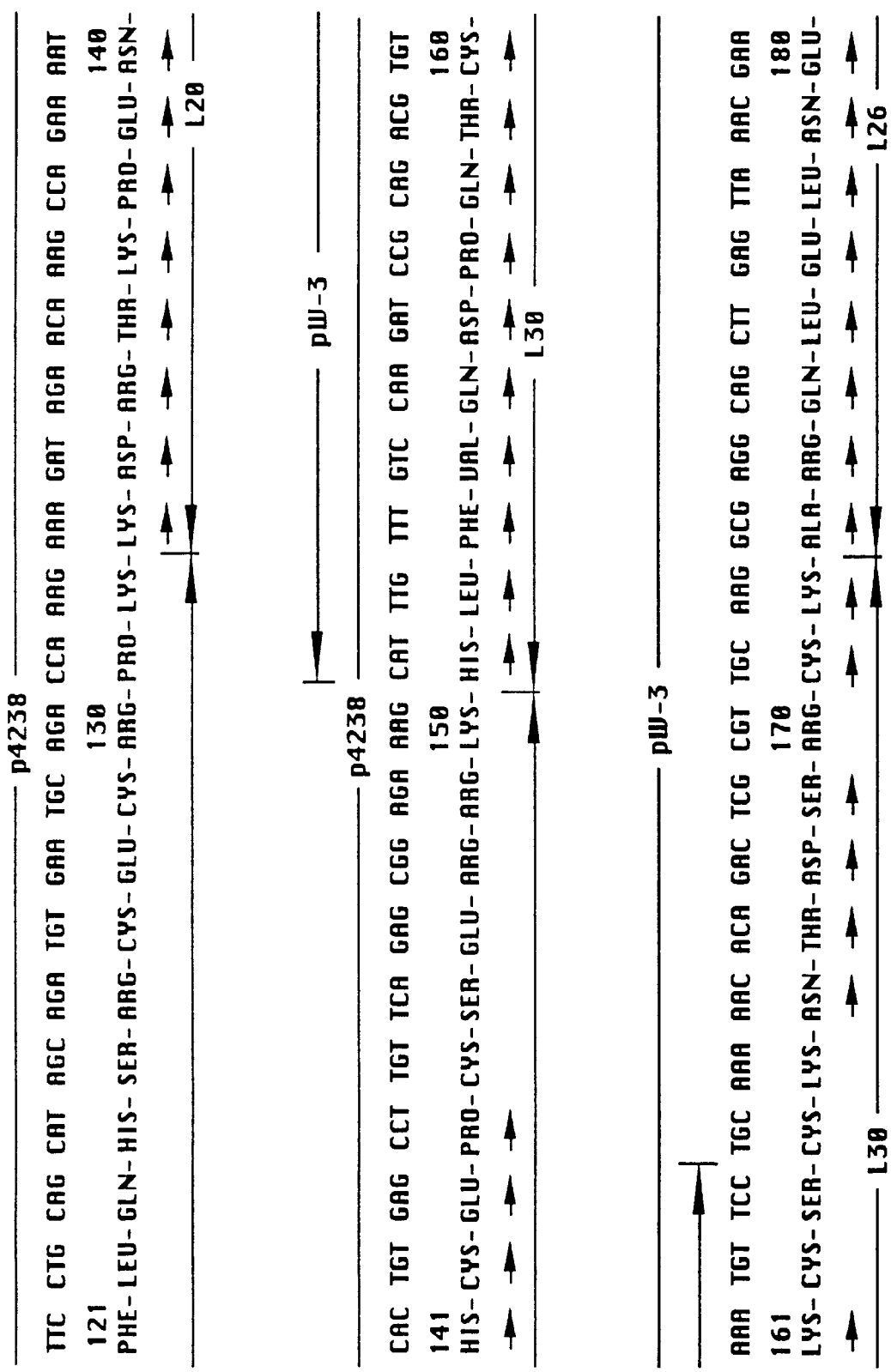
Figure 5C:
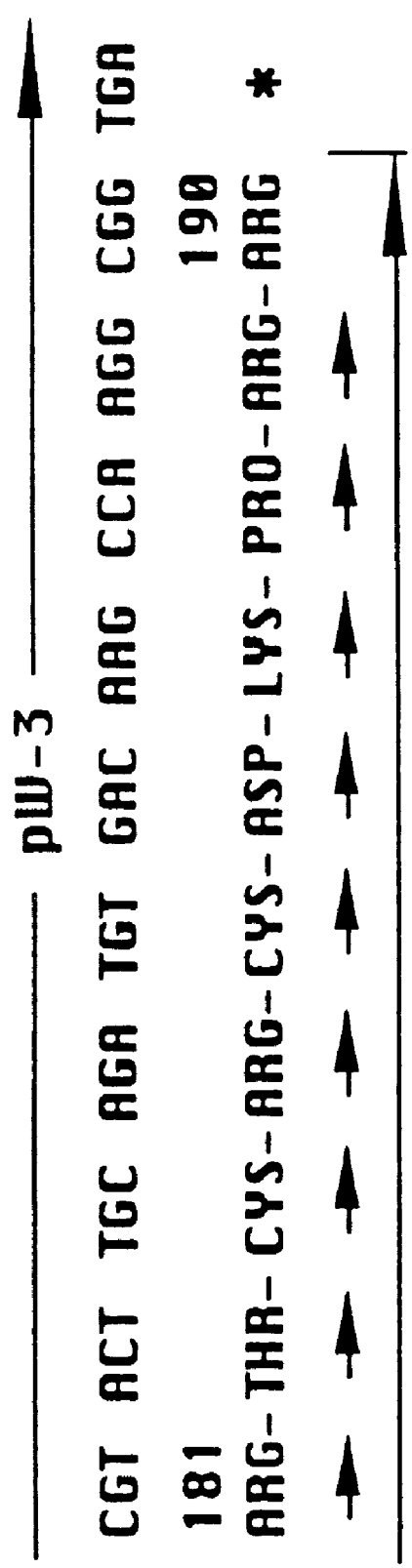

The SalI fragment was then ligated into SalI cut pGEM3Zf (+). The ligation mix was used to transform *E. coli* XL-1 blue. Plasmid DNA was isolated from white transformants and sequenced by the dideoxy chain termination method. The base sequence is shown in FIGS. 5 through 5C.

Cloning and Sequencing of Alternative Forms of VEGF A cDNA

Based on the sequence obtained from the p5–15 and pW-3 clones, two specific PCR primers were synthesized;
oligo 5'C.

5' TTTGTCGACAACCATGAACTTTCTGC 3' and oligo 181

5' TTTGTCGACGGTGAGAGGTCTAGTTC 3'. These primers were used together to amplify multiple cDNAs encoding alternative forms of the VEGF A subunit.

Preparative PCR Reaction

50 μl 10× buffer

80 μl 1.25 mM each stock of dATP, dCTP, dGTP, and dTTP

10 μl first strand GS-9L cDNA

10 μl 300 pMoles oligo 5'C

10 μl 300 pMoles oligo 181

2.5 μl 15 units Amplitaq DNA polymerase 337.5 μl water

Reaction conditions 94° C., 1'; 58° C., 2'; 72° C., 3'; 40 cycles.

The PCR product was extracted with phenol/chloroform, concentrated by Centricon 30 spin columns, precipitated by ethanol, and digested with restriction endonuclease SalI, and ligated into SalI cut pGEM3Zf(+). The ligation mix was used to transform *E. coli* XL-1 blue. Plasmid DNA was isolated from white transformants and sequenced by the dideoxy chain termination method. Three sets of clones were identified. Clone #12 encoded the 164 amino acid secreted form of VEGF A subunit identical to that shown in FIG. 4. The 164 amino acid form of VEGF A subunit is that amino acid sequence runing continuously from $Ala^{27}$ to $Arg^{190}$. Clone #14 has a 135 base pair deletion between the second base of the $Asn^{140}$ codon and the third base of the $Arg^{184}$ codon. This clone thus encodes a 120 amino acid secreted form of the VEGF A subunit with the conversion of $Asn^{140}$ to $Lys^{140}$. The 120 amino acid form of VEGF A subunit runs from $Ala^{27}$ to $Asn^{140}$, which becomes $Lys^{140}$ and does not begin until $Cys^{185}$, this form also finishes at $Arg^{190}$. Clone #16 has a 72 base pair insertion between the second and third base of the $Asn^{140}$ codon. This clone thus encodes a 188 amino acid secreted form of the VEGF A subunit with the conversion of $Asn^{140}$ to $Lys^{140}$. The nucleotide sequence and the deduced amino acid sequence of this insertion is:

Lys Lys Ser Val Arg Gly Lys Gly Lys Gly A AAA TCA GTT CGA GGA AAG GGA AAG GGT

Gln Lys Arg Lys Arg Lys Lys Ser Arg CAA AAA CGA AAG CGC AAG AAA TCC CGG

Phe Lys Ser Trp Ser Val TTT AAA TCC TGG AGC GT

EXAMPLE 10

Cloning and Sequencing of the VEGF II B Subunit

PCR Amplification Cloning and Sequencing of pYG

Two degenerate oligonucleotides were synthesized in order to amplify the cDNA encoding the peptide sequences of VEGF II B on Lys C fragment L50. These oligonucleotides were:

YI
5'TTTGTCGACATA[TC]AT[TCA]GC[N]GA[TC]GA[AG]C 3'

GC
5' TTTGTCGACTC[AG]TC[AG]TT[AG]CA[AG]CA[N]CC 3' where N=ACGT

RNA was isolated from GS-9L cells using the Fast Track RNA isolation kit from Invitrogen and the protocol provided. First strand cDNA synthesis was performed as follows; 1 μg of GS-9L poly $A^+$RNA was annealled to 1 μg of adapter primer TA17,

5'GACTCGAGTCGACATC-GATTTTTTTTTTTTTTTTT 3', by incubating in a volume of 10 μl at 70° C. for 5 min followed by cooling to room temperature. To this reaction was added:

3.0 μl water 2.5 μl 10× buffer (500 mM Tris-HCl, pH 8.3, 750 mM KCl, 100 mM $MgCl_2$, 5 mM spermidine)

2.5 μl 100 mM DTT 2.5 μl 10 mM each dATP, dGTP, dCTP, dTTP 0.6 μl 15 units RNasin 2.5 μl 40 mM Na pyrophosphate 1.5 μl 15 units reverse transcriptase and the reaction was incubated at 42° C. for 1 hr, then diluted to 1 ml in 10 mM Tris-HCl, 1 mM EDTA, pH 7.5.

PCR Reactions

Primary reaction (50 μl)

5 μl 10× buffer from Perkin Elmer Cetus Gene Amp kit

8 μl 1.25 mM each stock of dATP, dCTP, dGTP, and dTTP

1 μl first strand GS-9L cDNA

1 μl 50 pMoles oligo YI

1 μl 50 pMoles oligo GC 0.25 μl 1.25 units Amplitaq DNA polymerase 33.75 μl water Reaction conditions, 40 cycles of 94° C., 1'; 50° C., 2'; 72° C., 2'.

Prep scale reaction:

60 μl 10× buffer

96 μl 1.25 mM each stock of dATP, dCTP, dGTP, and dTTP

12 μl first strand 659L cDNA

12 μl 500 pMoles oligo YI

12 μl 500 pMoles oligo GC

3 μl 15 units Amplitaq DNA polymerase

405 μl water

Reaction conditions 94° C., 1'; 50° C., 2'; 72° C., 2' 40 cycles.

The PCR product was concentrated by Centricon 30 spin columns and digested with restriction endonuclease SalI. The SalI fragment was then ligated into SalI cut pGEM3Zf (+). The ligation mix was used to transform *E. coli* XL-1 blue. Plasmid DNA was isolated from white transformants and sequenced by the dideoxy chain termination method.

PCR Amplification Cloning and Sequencing of p3V2

Based on the sequence obtained from the pYG clones, a specific PCR primer was synthesized;

oligo HP

5' TTTGTCGACACACCCTAATGAAGTGTC 3'.

This primer was used in combination with oligo A17

5' GACTCGAGTCGACATCG 3' to amplify the cDNA encoding the COOH terminus of the VEGF II B subunit using the 3' RACE technique described by Frohman et al., Proc. Natl. Acad. Sci. USA 85:8998–9002 (1988).

Preparative PCR reaction:

60 µl 10× buffer from Perkin Elmer Cetus Gene Amp Kit

12 µl first strand 659L cDNA

96 µl 1.25 mM each of dATP, dCTP, dGTP, and dTTP

12 µl 300 pMoles oligo A17

12 µl 300 pMoles oligo HP

3 µl 15 units Amplitaq DNA polymerase

405 µl water

Reaction conditions: 1 cycle of 94° C., 1'; 58° C., 2'; 72° C., 2'; followed by 40 cycles 94° C., 1', 58° C., 2' and 72° C., 2'.

The PCR product was concentrated by Centricon 30 spin columns, precipitated with ethanol and digested with restriction endonuclease SalI. The SalI fragment was then ligated into SalI cut pGEM3Zf(+). The ligation mix was used to transform E. coli XL-1 blue. Plasmid DNA was isolated from white transformants and sequenced by the dideoxy chain termination method.

PCR Amplification Cloning and Sequencing of p5V2

Based on the sequence of pYG clones, two specific PCR primers were synthesized;

oligoVL'

5' TTTGTCGACAACAGCGACTCAGAAGG 3' and oligoVS'

5' TTTGTCGACACTGAATATATGAGACAC 3'.

These primers were used in combination with oligo A17

5' GACTCGAGTCGACATCG 3' to amplify the cDNA encoding the amino terminus of the VEGF II B subunit using the 5' RACE technique described by Frohman et al., supra. Oligo 151 was synthesized in order to prime cDNA from GS-9L RNA.

Oligo 151 is

5' CTTCATCATTGCAGCAGC 3'.

Ploy A+RNA was isolated from GS9L cells using the Fast Track RNA isolation kit from Invitrogen using the protocol provided. First strand cDNA synthesis was performed as follows:

One µg of GS-9L RNA was annealled to 1 µg of oligo151 by incubating in a volume of 6 µl at 70° C. for 5' followed by cooling to room temperature. To this reaction was added:

1.5 µl 10× buffer (500 mM Tris-HCl, pH 8.3, 750 mM KCl, 100 mM MgCl$_2$, 5 mM spermidine)

2.5 µl 10 mM DTT 2.5 µl 10 mM each dATP, dGTP, dCTP, and dTTP 0.6 µl 25 units RNasin 2.5 µl 40 mM Na pyrophosphate 9.5 µl 20 units diluted reverse transcriptase The reaction was incubated at 42° C. for 1 hr.

Excess oligo 151 was removed by Centricon 100 spin columns and the 5' end of the cDNA was tailed by the addition of dATP and terminal transferase. The tailed cDNA was diluted to a final volume of 150 µl in 10 mM Tris-HCl, 1 mM EDTA, pH 7.5.

PCR Reactions

Primary reaction (50 µl)

5 µl 10× buffer from Perkin Elmer Cetus GeneAmp Kit

8 µl 1.25 mM each stock of dATP,dCTP,dGTP, and dTTP

5 µl first strand GS-9L cDNA primed with oligo151 and tailed 1 µl 25 pMoles oligo VL'

1 µl 25 pMoles oligo A17

1 µl 10 pMoles oligo TA17

0.25 µl 1.25 units Amplitq DNA polymersase 28.75 µl water

Reaction conditions; 1 cycle 94° C.,1'; 58° C., 2'; 72° C., 40' then 40 cycles of 94° C., 1'; 58° C., 2'; 72° C., 2'.

Prep scale secondary reaction:

100 µl 10× buffer

160 µl 1.25 mM each stock of dATP, dCTP, dGTP, and dTTP

10 µl primary PCR reaction

20 µl 500 pMoles oligo VS'

20 µl 300 pMoles oligo A17

5 µl 25 units Amplitaq DNA polymerase

685 µl water

Reaction conditions: 94° C., 1'; 58° C., 2'; 72° C., 2' 30 cycles.

The PCR product was extracted with phenol/chloroform, concentrated by Centricon 30 spin columns, precipitated by ethanol, and digested with restriction endonuclease SalI. The SalI fragment was purified on 4% Nu-Sieve Agarose gel then ligated into SalI cut pGEM3Zf(+). The ligation mix was used to transform E. coli XL-1 blue. Plasmid DNA was isolated from white transformants and sequenced by the dideoxy chain termination method.

PCR Amplification, Cloning and Sequencing of pCV2 and pCV2.1

Based on the sequences of the p3V2 and p5CV2 clones, two specific PCR primers were synthesized;

oligo 5'CV2.1

5' TTTGTCGAC[N][N]GCAGGTCCTAGCTG 3' and oligo 3'CV2

5' TTTGTCGAC[N][N]CTAATAAATAGAGGG 3'.

These primers were used together to amplify the CDNA encoding the VEGF B subunit.

Preparative PCR Reaction

40 µl 10× buffer

64 µl 1.25 mM each dATP, dTTP, dGTP, and dCTP

8 µl first strand GS-9L cDNA

8 µl 200 pMoles 5'CV2.1

8 µl 8 µl 200 pMoles 3'CV2

2 µl 10 units Amplitaq DNA polymerase

270 µl water

Reaction conditions: 94° C., ', 58° C., 2', 72° C., 2'; 40 cycles.

The PCR product was extracted with phenol/chloroform, concentrated by Centricon 30 spin columns, precipitated by ethanol, and digested with restriction endonuclease Sal I, and ligated into Sal I cut pGEM3Zf(+). The ligation mix was used to transform E. coli XL-1 blue. Plasmid DNA was isolated form white transfromants and sequenced by the dideoxy chain termination method. Two sets of clones were identified, one encoded a 135 amino acid sequence and the other encoded a 115 amino acid sequence, see FIGS. 6 through 6B and FIGS. 7 through 7A respectively.

cDNA Cloning of VEGF B Subunit

The DNA and protein sequences for the amino terminus of the signal peptide of VEGF B was determined from a cDNA clone isolated from a cDNA library constructed from GS-9L polyA$^+$ RNA.

First Strand Synthesis:

Anneal 15.6 µl (5 ug) GS-9L polyA$^+$ RNA and 2.5 µl (2.5 ug) oligo dT-XbaI primer by heating to 70° C., 5' slow cool to room temperature. Add the following:

5.5 µl 10× buffer (500 mM Tris-HCl, pH 8.3 (42° C.), 750 mM KCl, 100 mM MgCl$_2$, 5 mM spermidine 5.5 µl 100 mM DTT 5.5 µl 10 mM each dATP, dTTP, dCTP, and dGTP
1.4 µl (55 units) RNasin
5.5 µl 40 mM Na pyrophosphate
13.5 µl 55 units AMV reverse transcriptase
Incubate at 42° C., 60'.
Second Strand Synthesis
Assemble reaction mix
50 µl first strand reaction
25 µl 10× buffer (500 mM Tris-HCl, pH7.2, 850 mM KCL, 30 mM $MgCl_2$, 1 mg/ml BSA, 100 mM $(NH_4)_2SO_4$
7.5 µl 100 mM DTT
25 µl mM NAD
6.5 µl (65 units) E. coli DNA Polymerase I
2.5 µl (2.5 units) E. coli DNA Ligase
2.5 µl (2 units) E. coli RNase H
135 µl water
Incubate at 14° C. for 2 hr and then incubate 70° C. for 10'. Add 1 ul (10 units) T4 DNA Polymerase, incubate at 37° C. for 10', add 25 µl 0.2 M EDTA, extract with phenol/chloroform, then precipitate by the addition of 0.5 volume of 7.5 M ammonium acetate and 3 volumes of ethanol, collect precipitate and resuspend in 20 µl of 10 mM Tris-HCl, pH 7.5, 1 mM EDTA.

cDNA Library Construction

The above cDNA was ligated into EcoR1/XbaI digested LambdaGEM-4 (Promega Biochemicals) after the addition of EcoR1 linkers and digestion with EcoR1 and XbaI. A cDNA library was amplified from ~50,000 independent clones.

Isolation of Rat VEGF B cDNA Clone:

The above cDNA library was screen by placque hybridization using pCV2 as a probe. Hybridization conditions were as follows:

5× SSC (1× SSC is 0.15 M NaCl, 0.015 M sodium citrate,
50% formamide
5× Denhardt's Solution (1% Ficoll, 1% polyvinylpyrrolidone, 1% bovine serum albumin)
0.15 mg/ml salmon sperm DNA
Hybridize overnight at 42° C.

Filters were washed 3 times in 2× SSC, 0.1% SDS at room temerature for 5', then 1 time in 1× SSC, 0.1% SDS at 50° C. for 30'. Positive clones were identified by autoradiography.

The DNA from phage #202 was digested with restriction endonuclease SpeI and the 1.1 kb band ligated into XbaI digested pGEM3Zf(+). The ligation mix was used to transform E. coli XL-1 blue. Plasmid DNA was isolated from white transformants and sequenced by the dideoxy chain termination method. The cDNA sequence and predicted amino acid sequence of the signal peptide are shown in FIGS. 6 through 6B and FIGS. 7 through 7A.

The entire nucleotide and amino acid sequence of the 115 amino acid form is shown in FIGS. 7 through 7A. The secreted protein starts at $Ala^{24}$ and continues to $Arg^{138}$. The entire nucleotide and amino acid sequence of the 135 amino acid form is shown in FIGS 7 through 7A. The secreted protein starts at $Ala^{24}$ and continues to $Leu^{158}$.

EXAMPLE 11

Further Separation of the VEGF II Heterodimer from the VEGF I Homodimer

Serum-free conditioned media from rat GS-9L glioma cells were generated, filtered and sequentially chromatographed on CM-Sephadex C-50 (Pharmacia) and Con A Sepharose lectin affinity (Pharmacia) columns at 4° C. as described for the purification of VEGF homodimers [Conn, G., Soderman, D. D., Schaeffer, M.-T., Wile, M., Hatcher, V. B. and Thomas, K. A., (1990) Proc. Natl. Acad. Sci. USA 87, 1323–1327] with the exception that media were conditioned by cells maintained in 3% oxygen rather than the ambient ~20% oxygen. All subsequent chromatographic steps were performed at 20–22° C. Protein specifically eluted from the lectin affinity column was loaded onto a 25×0.46 cm poly (aspartic acid) WCX HPLC column (Nest Group) pre-equilibrated in 50 mM sodium phosphate, pH 6.0, and eluted with a 45 min 0 to 1 M NaCl linear gradient at a flow rate of 0.75 ml/min monitoring absorbance at 280 nm. VEGF was purified from the second peak of mitogenic activity as described [Conn, G., Soderman, D. D., Schaeffer, M.-T., Wile, M., Hatcher, V. B. and Thomas, K. A., (1990) Proc. Natl. Acad. Sci. USA 87, 1323–1327]. The first peak of mitogenic activity was pooled, loaded onto a 5×0.46 cm Vydac $C_4$ RP-HPLC column (The Separations Group) equilibrated in 10 mM TFA and eluted with a 60 min linear gradient of 0 to 67% acetonitrile at a flow rate of 0.5 ml/min monitoring absorbance at 210 nm. Mitogenically active fractions were pooled and re-chromatographed (Smart System, LKB) using a 5×0.1 cm $C_4$ microbore column with a linear 60 min gradient from 0 to 50% acetonitrile at a flow rate of 35 µl/min to yield pure VEGF II (AB) heterodimers.

Homodimeric VEGF BB was initially fractionated by sequential chromatography on CM-Sephadex C-50, Con A Sepharose lectin affinity and poly(aspartic acid) WCX HPLC columns as described for the VEGF I (AA) homodimer and VEGF II (AB) heterodimer purification. Further fractionation of homodimeric VEGF BB relied on the identification of immunocrossreactive protein by Western analysis using an antisera made to a synthetic polypeptide corresponding to amino acid residues 30–50 conjugated to a tuberculin-purified protein derivative as described [Fallon, J. H., DiSalvo, J., Loughlin, S. E., Gimenez-Gallego, G., Seroogy, K. B., Bradshaw, R. A., Morrison, R. S., Ciofi, P. and Thomas, K. A. (1992) Growth Factors 6, 139–157]. A second antisera was made to a synthetic polypeptide identical in sequence to residues 1–24 of VEGF I (AA) homodimers. These two antisera were used to identify chromatographic fractions containing either one or both of the VEGF B and A subunits. Fractions from the poly(aspartic acid) column that contained VEGF B but not VEGF A immunocrossreactive bands were pooled and chromatographed by sequential fractionation on a 5×0.46 cm Vydac $C_4$ RP-HPLC column followed by a 5×0.1 cm $C_4$ microbore column as described for the heterodimer purification.

Figure 8A:
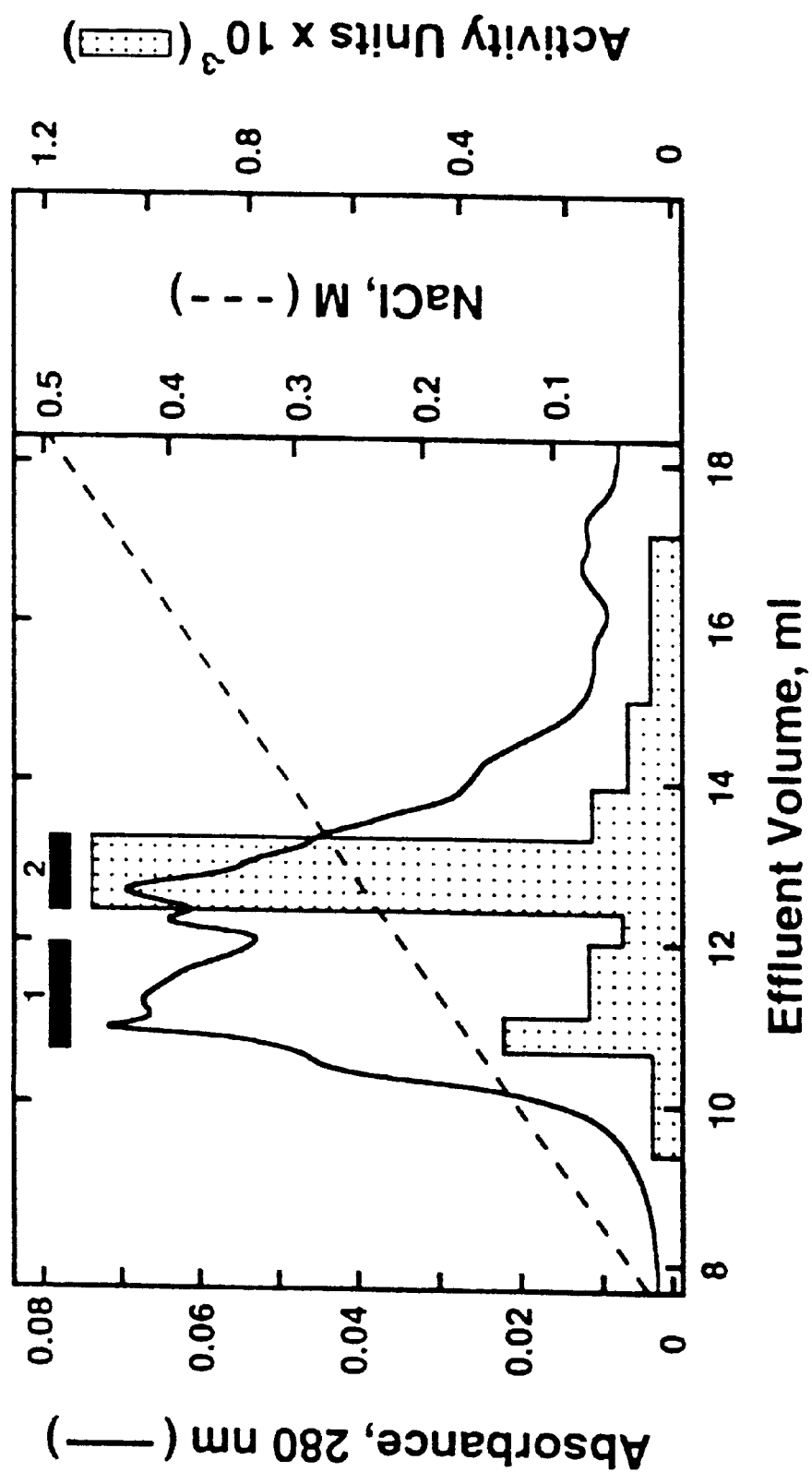
FIG. 8 Panels A, B, and C. (A) Active fractions were pooled, loaded onto a poly(aspartic acid) WCX HPLC column in 50 mM sodium phosphate, pH 6.0, and eluted at 0.75 ml/min with a linear gradient of 0 to 1 M NaCl. Two peaks of human umbilical vein endothelial (HUVE) cell mitogenic activity were observed and each pooled (horizontal bars). Material in pool 2 was purified to yield homodimeric VEGF I. (B) Fractions from the first active peak were combined (pool 1), loaded onto a $C_4$ reversed phase HPLC column equilibrated in 10 mM trifluoroacetic acid (TFA) and eluted with a linear gradient of 0–67% acetonitrile. (C) Mitogenically active fractions were again pooled and re-chromatographed using a microbore $C_4$ column equilibrated in 10 mM TFA and eluted with a linear gradient of 0–50% acetonitrile.
Figure 8B:
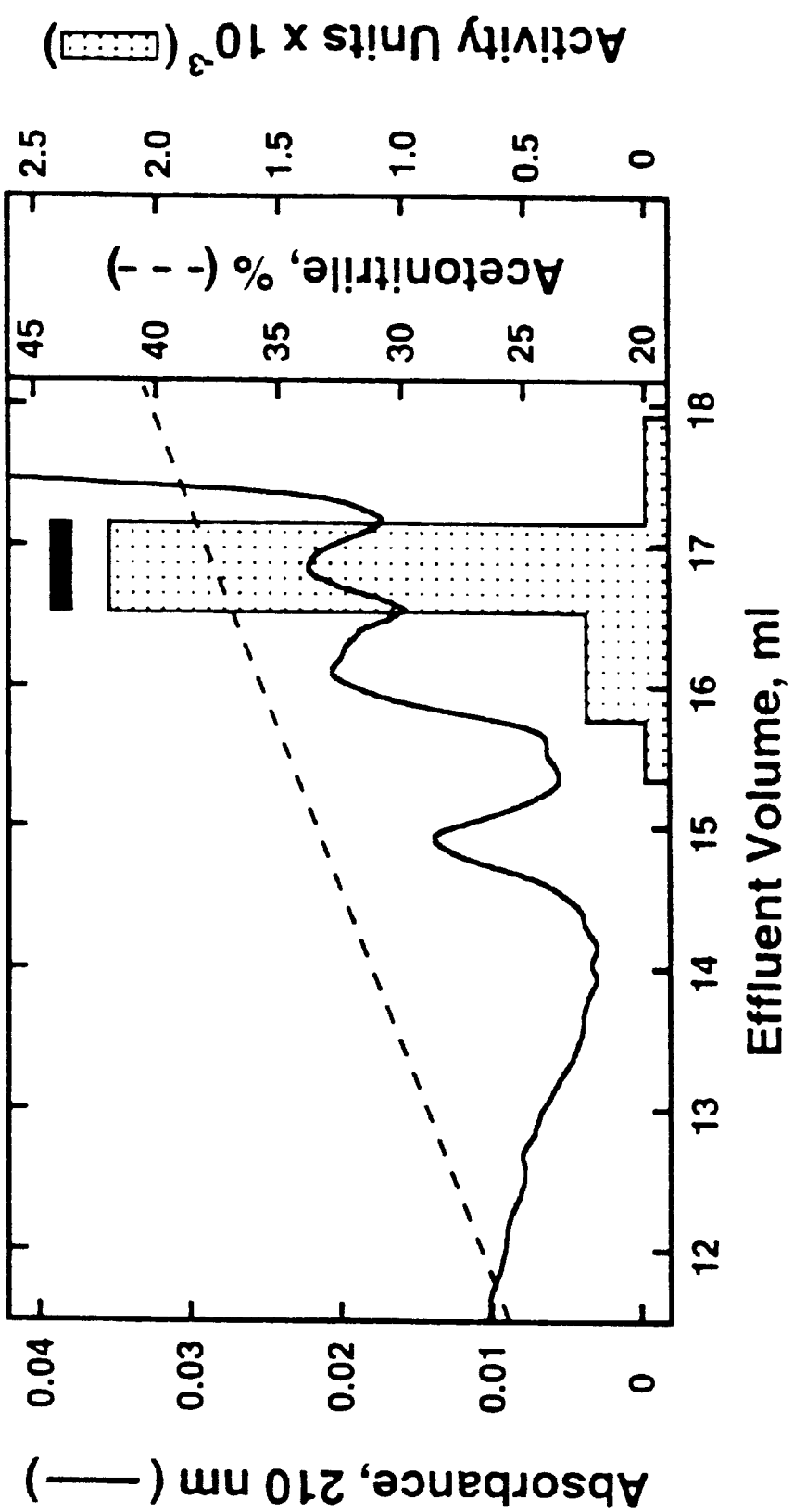
Figure 8C:
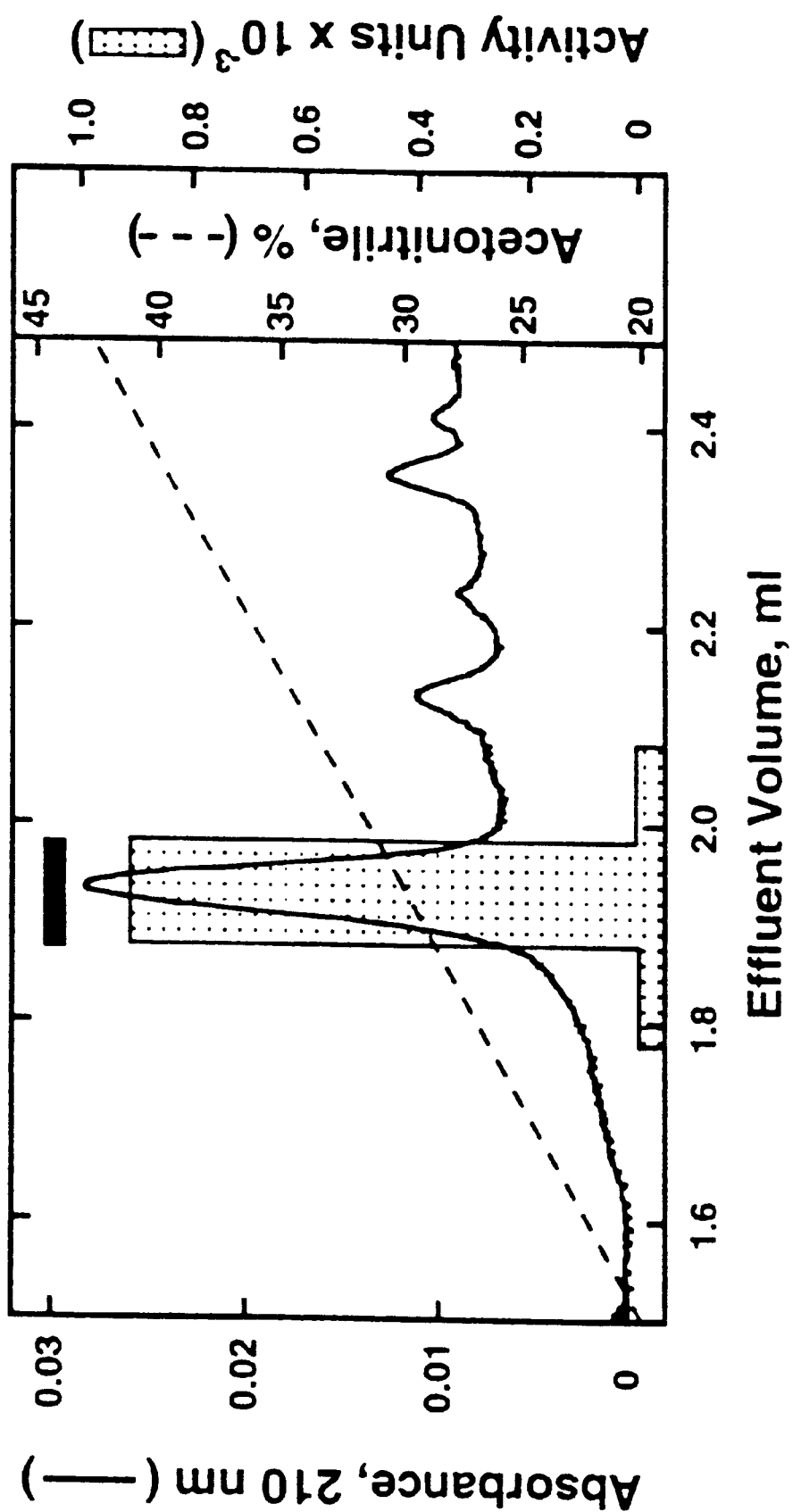

Conditioned media of rat GS-9L glioma cells were fractionated on CM-Sephadex C-50 and Con A Sepharose as described for the original purification of homodimeric VEGF I (AA) [Conn, G., Soderman, D. D., Schaeffer, M.-T., Wile, M., Hatcher, V. B. and Thomas, K. A., (1990) Proc. Natl. Acad. Sci. USA 87, 1323–1327]. Protein specifically eluted from the lectin column was resolved into two peaks of mitogenic activity, the second of which (FIG. 8 panel A, pool 2) was further fractionated to yield pure homodimeric VEGF. The protein mitogen in the first of the two activity peaks (FIG. 8 panel A, pool 1) has now also been purified to homogeneity by $C_4$ RP-HPLC (FIG. 8 panel B and FIG. 8 panel C) yielding 150–300 ng of pure protein (denoted VEGF II) per liter of conditioned medium.

Figure 9A:
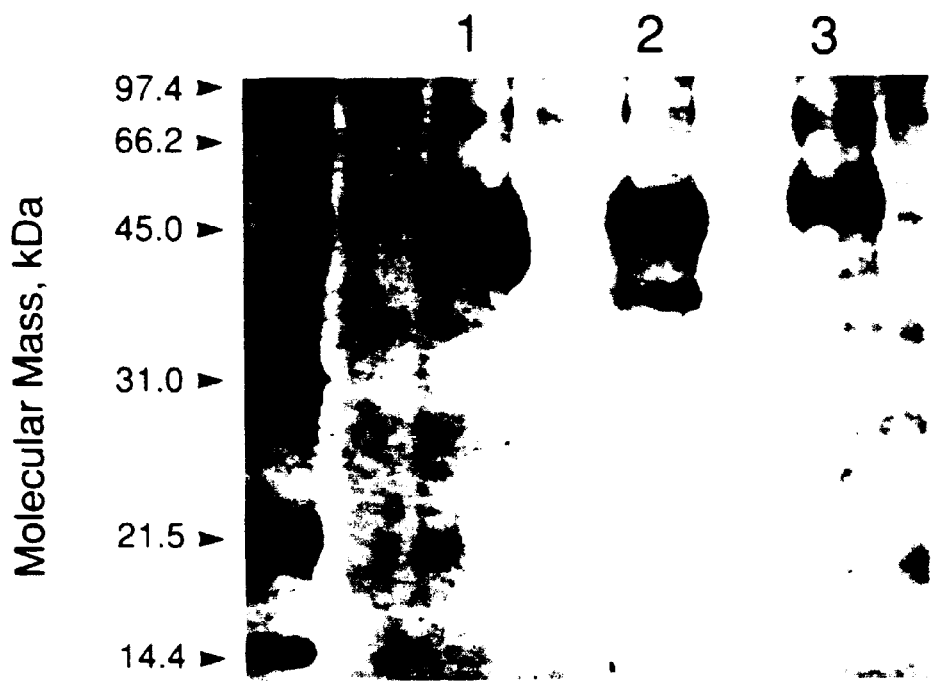
FIG. 9 Panels A, and B. Purities of VEGF I (AA), VEGF II (AB) and VEGF BB dimers (100 ng each) were determined by electrophoresis through 14% polyacrylamide SDS gels under non-reducing (A) and reducing (B) conditions followed by silver staining: left side, molecular mass standards; lane 1, VEGF I (AA); lane 2, VEGF II (AB); lane 3, VEGF BB.
Figure 9B:
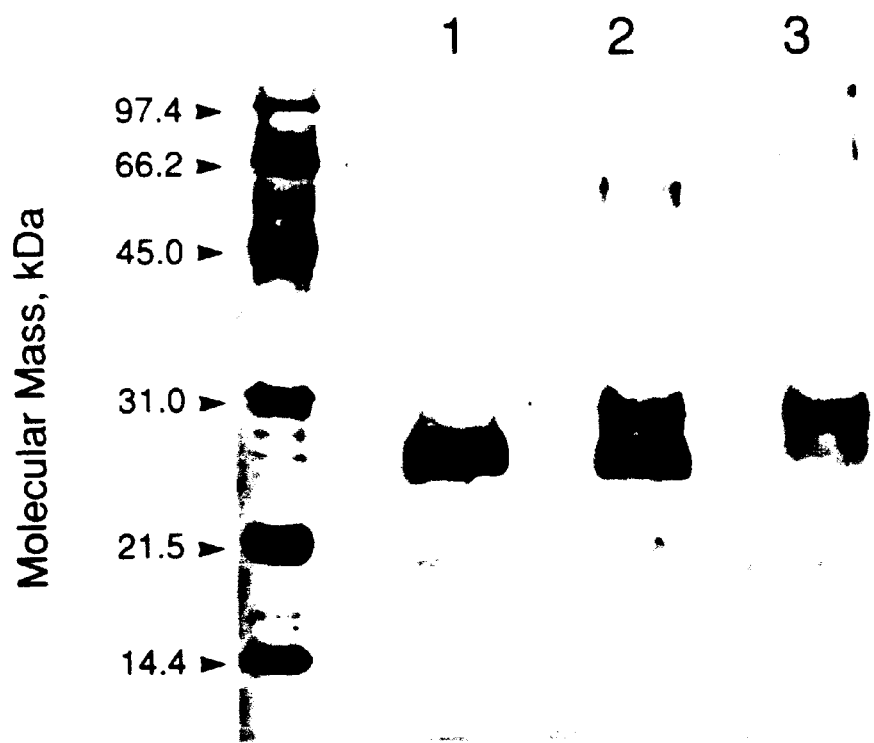
Figure 10A:
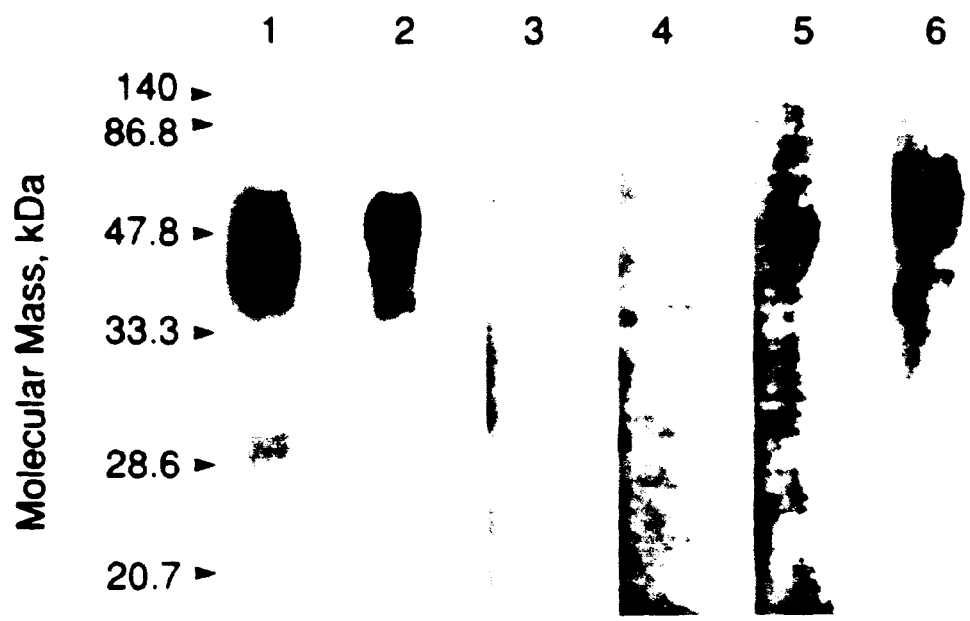
FIG. 10 Panels A, and B. Pure VEGF I (AA), VEGF II (AB) and VEGF BB dimers (100 ng each) were analyzed using subunit specific antisera after electrophoresis through 14% polyacrylamide SDS gels under non-reducing (A) and reducing (B) conditions, followed by electrophoretic transfer to Immobilon-P polyvinylidene difluoride membranes. Pure VEGF I (AA) (Lane 1), VEGF II (AB) (Lane 2) and VEGF BB (Lane 3) were probed with a 1/1000 dilution of VEGF A subunit specific antisera. Additionally, VEGF I (AA) (Lane 4), VEGF II (AB) (Lane 5) and VEGF BB (Lane 6) were probed with a 1/1000 dilution of VEGF B subunit specific antisera. Bound antibody was incubated with $^{125}$I-protein-A followed by overnight exposure and visualization using a Phosphorimager.
Figure 10B:
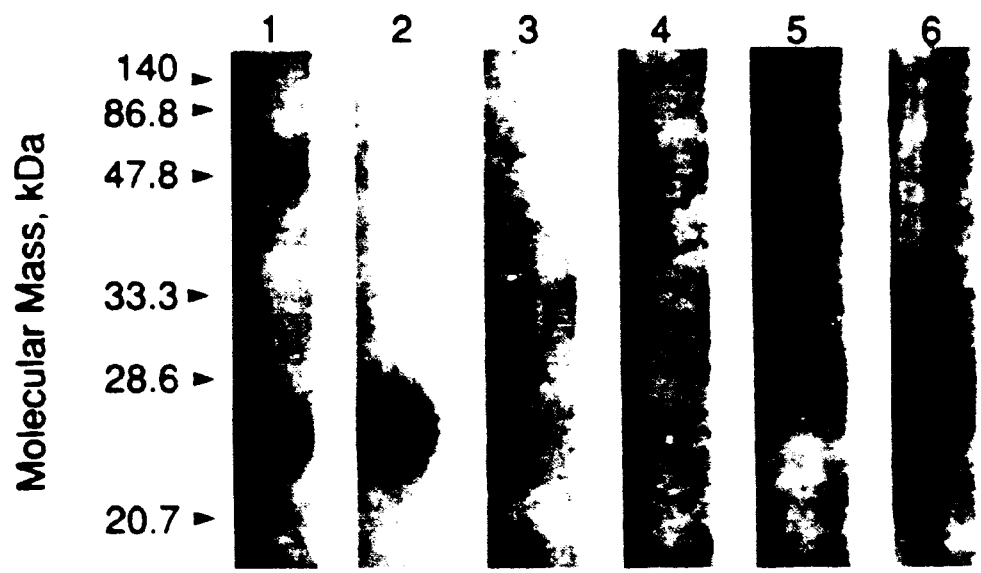

Compared to homodimeric VEGF I that has an apparent nonreduced mass of 43.5 kDa by this purification, the newly purified non-reduced VEGF II mitogen migrates as major 49.5 kDa and trace ~40 kDa bands (FIG. 9 panel A, lanes 1 and 2). Small differences in mass between this and the preceding purification can be attributable to differences in carbohydrate content. On reducing SDS/PAGE pure VEGF I homodimer migrates at its subunit mass of 27 kDa whereas this novel mitogen separates into two principal bands of 27 and 31 kDa (FIG. 9 panel B, lanes 1 and 2). Immunocross-reactive VEGF A subunit was demonstrated in both nonreduced proteins (FIG. 10 panel A, lanes 1 and 2) and to correspond to the reduced 27 kDa but not the 31 kDa bands (FIG. 10 panel B, lanes 1 and 2).

Figure 11:
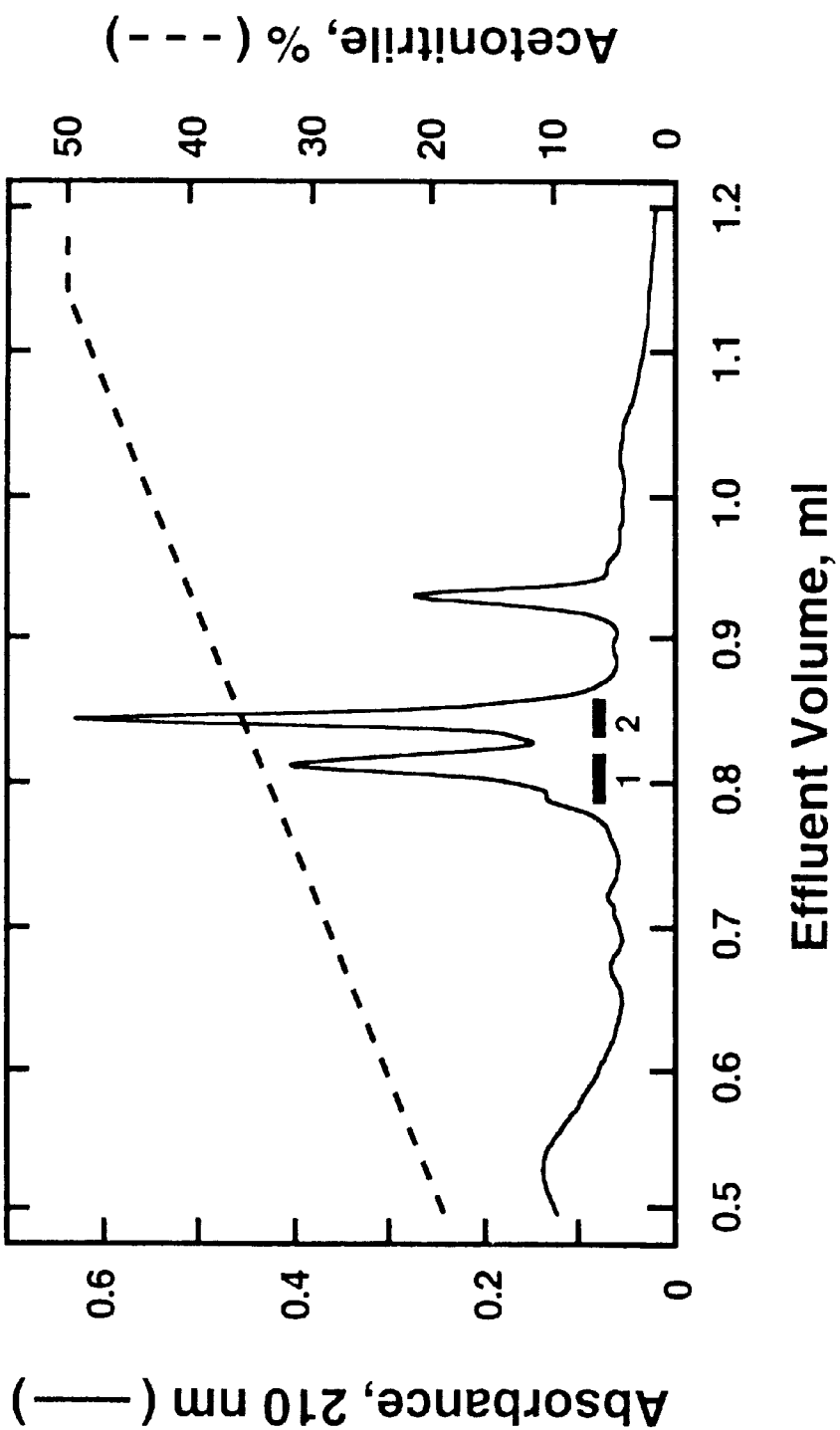
FIG. 11. Reduced and carboxymethylated VEGF II (AB) heterodimer subunits were purified on a microbore $C_4$ reversed-phase HPLC column equilibrated in 10 mM TFA and eluted with a 0–50% linear gradient of acetonitrile. The third major peak, eluting at an effluent volume of ~9.3 ml, was present in the reagent blank. Peak 1 was subsequently determined by amino terminal and peptide sequencing to correspond to the VEGF B subunit and peak 2 was identified to be the VEGF A subunit.

These two reduced and carboxymethylated polypeptides derived from the 49.5 kDa protein were also chromatographically resolved as peaks of virtually identical absorbance (area ratio of 1.00:1.03) at 210 nm eluted from a $C_4$ RP-HPLC column (FIG. 11). The second of the two eluted protein peaks was confirmed by N-terminal and polypeptide sequencing to be the previously identified [Conn, G., Bayne, M., Soderman, D. D., Kwok, P. W., Sullivan, K. A., Palisi, T. M., Hope, D. A. and Thomas, K. A. (1990) *Proc. Natl. Acad. Sci. USA* 87, 2628–2632] 164 amino acid subunit present in VEGF I homodimers. However, the first peak, designated VEGF B, was distinct by both N-terminal amino acid sequencing and sequence analysis of a family of polypeptides purified on a $C_{18}$ reversed phase HPLC column from a Lys-C digest (FIGS. 6 through 6B). Therefore, this newly purified mitogen appears to be a previously unknown heterodimer composed of VEGF A and B subunits.

What is claimed is:

1. A method of stimulating angiogenesis or wound healing through vascular repair, neovascularization, or both, by administering to a patient a pharmaceutically effective amount of mammalian vascular endothelial growth factor II wherein the growth factor comprises:
   a) an A subunit, wherein said A subunit is selected from the group consisting of a 188 amino acid mature form of an A subunit, wherein said 188 amino acid mature form has the amino acid sequence shown in FIGS. 5 through 5C from Ala 27 to Arg 190 with the substitution of Asn 140 to Lys 140 and the insertion of the amino acid sequence Lys-Ser-Val-Arg-Gly-Lys-Gly-Lys-Gly-Gln-Lys-Arg-Lys-Arg-Lys-Lys-Ser-Arg-Phe-Lys-Ser-Trp-Ser-Val between Lys 140 and His 141; a 164 amino acid mature form of an A subunit, wherein said 164 amino acid mature form has the amino acid sequence shown in FIGS. 5 through 5C from Ala 27 to Arg 190; and a 120 amino acid mature form of an A subunit, wherein said 120 amino acid mature form has the amino acid sequence shown in FIGS. 5 through 5C from Ala 27 to Arg 190 with the conversion of Asn 140 to Lys 140 and the deletion of the amino acid sequence from His 141 to Arg 184; and
   b) a B subunit, wherein said B subunit is a 135 amino acid mature form of a B subunit, wherein said 135 amino acid mature form has the amino acid sequence shown in FIGS. 6 through 6B from Ala 24 to Leu 158, and allelic variants thereof; with said growth factor being substantially free of other proteins.

2. A method of stimulating angiogenesis or wound healing through vascular repair, neovascularization, or both, by administering to a patient a pharmaceutically effective amount of mammalian vascular endothelial growth factor II wherein the growth factor comprises:
   a) an A subunit, wherein said A subunit is selected from the group consisting of a 188 amino acid mature form of an A subunit, wherein said 188 amino acid mature form has the amino acid sequence shown in FIGS. 5 through 5C from Ala 27 to Arg 190 with the substitution of Asn 140 to Lys 140 and the insertion of the amino acid sequence Lys-Ser-Val-Arg-Gly-Lys-Gly-Lys-Gly-Gln-Lys-Arg-Lys-Arg-Lys-Lys-Ser-Arg-Phe-Lys-Ser-Trp-Ser-Val between Lys 140 and His 141; a 164 amino acid mature form, of an A subunit, wherein said 164 amino acid mature form has the amino acid sequence shown in FIGS. 5 through 5C from Ala 27 to Arg 190; and a 120 amino acid mature form, of an A subunit, wherein said 120 amino acid mature form has the amino acid sequence shown in FIGS. 5 through 5C from Ala 27 to Arg 190 with the conversion of Asn 140 to Lys 140 and the deletion of the amino acid sequence from His 141 to Arg 184; and,
   b) a B subunit, wherein said B subunit is a 115 amino acid mature form of a B subunit, wherein said 115 amino acid mature form has the amino acid sequence shown in FIGS. 7 through 7A from amino acid Ala 24 to Arg 138, and allelic variants, thereof; with said growth factor being substantially free of other proteins.

3. A method of stimulating angiogenesis or wounds healing through vascular repair, neovascularization, or both, by administering to a patient a pharmaceutically effective amount of mammalian vascular endothelial growth factor II wherein the growth factor comprises:
   a) an A subunit, wherein said A subunit is selected from the group consisting of a 188 amino acid mature form, of an A subunit, wherein said 188 amino acid mature form has the amino acid sequence shown in FIGS. 5 through 5C from Ala 27 to Arg 190 with the substitution of Asn 140 to Lys 140 and the insertion of the amino acid sequence Lys-Ser-Val-Arg-Gly-Lys-Gly-Lys-Gly-Gln-Lys-Arg-Lys-Arg-Lys-Lys-Ser-Arg-Phe-Lys-Ser-Trp-Ser-Val between Lys 140 and His 141, a 164 amino acid mature form, of an A subunit, wherein said 164 amino acid mature form has the amino acid sequence shown in FIGS. 5 though 5C from Ala 27 to Arg 190; and a 120 amino acid mature form of an A subunit, wherein said 120 amino acid mature form has the amino acid sequence shown in FIGS. 5 through 5C from Ala 27 to Arg 190 with the conversion of Asn 140 to Lys 140 and the deletion of the amino acid sequence from His 141 to Arg 184; and
   b) a B subunit, wherein a mature form of said B subunit is from 115 amino acids to 135 amino acids in length, wherein said mature form has a contiguous amino acid sequence shown in FIGS. 6 through 6B starting at Ala 24 and ending between Arg 138 and Leu 158, inclusive, and allelic variants, thereof, with said growth factor being substantially free of other proteins.

4. A method of stimulating angiogenesis or wound healing through vascular repair, neovascularization, or both, by administering to a patient a pharmaceutically effective amount of mammalian vascular endothelial growth factor II wherein the growth factor comprises either a heterodimer or homodimer of a first and second B subunit, wherein each of said first and second B subunits is independently selected from the group consisting of a 135 amino acid mature form having the amino acid sequence shown in FIGS. 6 through 6B from Ala 24 to Leu 158, a 115 amino acid mature form having the amino acid sequence shown in FIGS. 7 through 7A, from Ala 24 to Arg 138, and allelic variants thereof; with said heterodimer or homodimer being substantially free of other proteins.

5. A method of stimulating angiogenesis or wound healing through vascular repair, neovascularization, or both, by administering to a patient a pharmaceutically effective amount of mammalian vascular endothelial growth factor II wherein the growth factor comprises either a heterodimer or homodimer of a first and second B subunit, wherein each of said first and second B subunits comprises a mature form from 115 amino acids in length to 135 amino acids in length, wherein said mature form has a contiguous amino acid sequence shown in FIGS. 6 through 6B starting at Ala 24 and ending between Arg 138 and Leu 158, inclusive, and allelic variants thereof, with said growth factor being substantially free of other proteins.

* * * * *